(12) United States Patent
Yang et al.

(10) Patent No.: US 12,005,129 B2
(45) Date of Patent: Jun. 11, 2024

(54) IMAGING COMPOSITIONS

(71) Applicant: THE PENN STATE RESEARCH FOUNDATION, University Park, PA (US)

(72) Inventors: Jian Yang, Arlington, TX (US); Dingying Shan, State College, PA (US); Nanyin Zhang, State College, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 279 days.

(21) Appl. No.: 16/337,501

(22) PCT Filed: Oct. 6, 2017

(86) PCT No.: PCT/US2017/055509
§ 371 (c)(1),
(2) Date: Mar. 28, 2019

(87) PCT Pub. No.: WO2018/067913
PCT Pub. Date: Apr. 12, 2018

(65) Prior Publication Data
US 2019/0282713 A1    Sep. 19, 2019

Related U.S. Application Data

(60) Provisional application No. 62/404,792, filed on Oct. 6, 2016.

(51) Int. Cl.
*A61K 9/00*    (2006.01)
*A61K 49/00*    (2006.01)
(Continued)

(52) U.S. Cl.
CPC ........ *A61K 49/126* (2013.01); *A61K 49/0002* (2013.01); *A61K 49/0054* (2013.01); *A61K 49/085* (2013.01); *A61K 49/105* (2013.01)

(58) Field of Classification Search
CPC .................................................... A61K 49/126
See application file for complete search history.

(56) References Cited

U.S. PATENT DOCUMENTS

| 2007/0269382 A1 | 11/2007 | Santra et al. |
| 2016/0137776 A1 | 5/2016 | Yang et al. |
| 2016/0206759 A1 | 7/2016 | Kataoka et al. |

OTHER PUBLICATIONS

Banik, Polymeric nanoparticles: the future of nanomedicine, WIREs Nanomed Nanobiotechnol, 2016, 8, 271-299 (Year: 2016).*
(Continued)

*Primary Examiner* — Paul W Dickinson
(74) *Attorney, Agent, or Firm* — Meunier Carlin & Curfman LLC

(57) ABSTRACT

In one aspect, compositions are described herein. In some embodiments, a composition described herein comprises, consists of, or consists essentially of an MRI-active or MRI-sensitive polymer or oligomer formed from (i) a non-alkoxylated and non-alkenoxylated citric acid, citrate, or ester/amide of citric acid, and optionally an alkoxylated or alkenoxylated citric acid, citrate, or ester/amide of citric acid, (ii) a polyol/polyamine such as a diol/diamine, (iii) a monomer comprising an MRI contrast agent, and (iv) an amino acid monomer. The polymer or oligomer may be photoluminescent and MRI-sensitive. In another aspect, imaging methods utilizing the compositions described herein are described. In another aspect, scaffolds, grafts, and films comprising, consisting of, or consisting essentially of the compositions described herein are described.

22 Claims, 18 Drawing Sheets

(51) Int. Cl.
*A61K 49/08* (2006.01)
*A61K 49/10* (2006.01)
*A61K 49/12* (2006.01)

(56) References Cited

OTHER PUBLICATIONS

Frullano, L. et al., "Multimodal MRI Contrast Agents," *J. Biol. Inorg. Chem.*, (2007) 12:939-949.
Rashid, H. Ur., et al. "Lanthanide(III) Chelates as MRI Contrast Agents: Brief Description," *J. Structural Chem.*, vol. 54, No. 1, pp. 223-249, 2013.
Tang, J., et al., "Macromolecular MRI Contrast Agents: Structures, Properties, and Applications," *Progress in Polymer Sci.*, 38 (2013) 462-502.
Laurent, S. et al., Chapter 6 MRI Applications: Classification According to Their Biodistribution and Table of Contents, MRI Contrast Agents: From Molecules to Particles, Springer e-book, pp. 112-125, 2017.
PCT International Search Report and Written Opinion dated Feb. 5, 2018 for PCT/US2017/055509.
U.S. Appl. No. 62/404,792, filed Oct. 6, 2016.
PCT/US2017/055509, filed Oct. 6, 2017, WO 2018/067913.

* cited by examiner

[Gd(DTPA-BMA)(H₂O)]2-(MAGNEVIST TM)

[Gd(DOTA)(G₂O)]-(DOTAREM TM)

[Gd(DTPA-BMA)(H₂O)] (OMNISCAN TM)

[Gd(DO3A-BUTROL)(H₂O)] (GADOVIST TM)

[Gd(HP-DOTA)(H₂O)] (ProHance TM)

Gd-DTPA, MAGNEVIST®, BAYER HealthCare, GERMANY

Gd-DTPA-BMA, OMNISCAN®, GE HealthCare, UK

Gd-DOTA, DOTAREM® GUERBET, FRANCE

Gd-HP-DO3A, Prohancer®, BRACCO, ITALY

Gd-DTPA-BMEA, OPTIMARK®, MALLINCKRODT, US

Gd-DO3A-BUTROL, GADOVIST®, BAYER HealthCare, GERMANY

Gd-EOB-DTPA, EOVIST®, BAYER HealthCare, GERMANY

Gd-BOPTA, MULTIHANCE®, BRACCO, ITALY

MS-325, AngioMARK®, VASOVIST®, EPIX, US

IMAGING COMPOSITIONS

CROSS REFERENCE TO RELATED APPLICATIONS

This application is a 35 U.S.C. § 371 National Stage filing of International Application No. PCT/US2017/055509, filed on Oct. 6, 2017, which claims priority to U.S. Provisional Application Ser. No. 62/404,792, filed Oct. 6, 2016.

FIELD

This invention relates to compositions comprising polymers or oligomers and methods of using such compositions. In particular, the invention relates to imaging compositions useful for magnetic resonance imaging (MRI) and methods of using such compositions in imaging applications, including MRI.

BACKGROUND

Non-invasive biomedical imaging has become an intensive focus of research in biomaterials and regenerative engineering. In tissue engineering literature, scaffold degradation in vivo is often predicted by the outcomes of in vitro degradation studies, but these studies often inaccurately predict actual degradation in vivo. Although it is well known that the scaffold degradation rate should match the rate of new tissue formation in tissue engineering, biomaterials designed to control the in vivo scaffold degradation rate remain empirical due to the lack of in vivo quantitative validation. It is imperative to find an in situ real-time method to facilitate tracking tissue regeneration and scaffold degradation processes non-invasively. In particular, biodegradable imaging tools that are effective at deep tissue depths, e.g., body tissue depths greater than about 2 cm, are desired.

SUMMARY

In one aspect, MRI-active or MRI-sensitive compositions are described herein. In some embodiments, the MRI-active or -sensitive compositions described herein comprise, consist of, or consist essentially of one or more citrate-containing polymers or oligomers that are MRI-active or, synonymously, MRI-sensitive. In some embodiments, the one or more MRI-sensitive citrate-containing polymers or oligomers have an MRI-contrast agent integrated into or pendant from their polymeric or oligomeric backbone. The one or more MRI-sensitive citrate-containing polymers or oligomers may be formed from one or more monomers that comprise an MRI contrast agent.

In some further embodiments, the compositions described herein may also be photoluminescent. For example, in addition to being MRI-sensitive, the compositions may be fluorescent in a wide range of wavelengths, such as in the near-infrared (NIR) region. In these further embodiments, the compositions described herein may comprise, consist of, or consist essentially of one or more citrate-containing polymers or oligomers that are active for magnetic resonance imaging and one or more citrate-containing polymers or oligomers that are photoluminescent or both MRI-sensitive and photoluminescent. These one or more citrate-containing polymers or oligomers that are photoluminescent or both MRI-sensitive and photoluminescent may be fluorescent in the NIR or both MRI-sensitive and fluorescent in the NIR.

Further, in some embodiments, the compositions described herein may be biodegradable. The compositions may, in some embodiments, comprise, consist of, or consist essentially of, a polymer or oligomer that is biodegradable. In some embodiments, at least one of the MRI-sensitive citrate-containing polymers, the photoluminescent citrate-containing polymers, and the MRI-sensitive and photoluminescent citrate-containing polymers is biodegradable.

In some further embodiments, the compositions described herein may further comprise nanoparticles dispersed in the polymers or oligomers. In some embodiments, the polymers or oligomers of the compositions described herein may be cross-linked to form a polymer network. The polymer network may comprise nanoparticles dispersed therein.

In some embodiments, a composition described herein comprises, consists, or consists essentially of a polymer or oligomer formed from the following: (i) a non-alkoxylated and non-alkenoxylated citric acid, citrate, or ester/amide of citric acid monomer, and optionally, an alkoxylated or alkenoxylated citric acid, citrate, or ester/amide of citric acid monomer; (ii) a polyol or polyamine monomer such as a diol or diamine; (iii) a monomer comprising an MRI-contrast agent; and (iv) an amino acid monomer. In some cases, a composition described herein comprises a polymer or oligomer formed from other reactants or monomers in addition to (i), (ii), and (iii) or (i), (ii), (iii), and (iv). For example, a composition can comprise, consist, or consist essentially of a polymer or oligomer formed from (i)-(iii) or (i)-(iv) and at least one of the following reactants or monomers: an amine-containing diol, a catechol-containing species, a polycarboxylic acid, an isocyanate, and a monomer or reactant comprising an alkyne moiety and/or an azide moiety. The catechol-containing species may be, in some embodiments, L-DOPA, D-DOPA, or 3,4-dihydroxyhydrocinnamic acid. The amine-containing diol may be, in some embodiments, methyl diethanolamine (MDEA). The carboxylic acid may be maleic acid, maleic anhydride, or fumaric acid. The amine may be a diamine. In some embodiments, the monomer or reactant comprising an alkyne moiety and/or an azide moiety may be a peptide, polypeptide, nucleic acid, or polysaccharide.

In another aspect, methods of imaging a biological environment using the MRI-sensitive compositions described herein are described. The methods comprise disposing the MRI-sensitive compositions in a biological environment.

In some embodiments, the method of imaging a biological environment may be an MRI method and may comprise the following additional steps: (1) exposing the biological environment to radio-frequency electromagnetic radiation while the biological environment is disposed in a magnetic field, thereby exciting hydrogen atoms of the biological environment, and then (2) detecting relaxation of the excited hydrogen atoms.

In some embodiments, the method of imaging a biological environment may comprise the disposing step and the following additional steps: (1) exposing the biological environment to electromagnetic radiation having a wavelength corresponding to an excitation wavelength of a photoluminescent moiety of the polymer or oligomer, and then (2) detecting light emitted by the luminescent moiety. In these embodiments, the disposed composition is an MRI-sensitive and photoluminescent composition, which may comprise citrate-containing polymers or oligomers as described herein that are photoluminescent or both MRI-sensitive and photoluminescent. The luminescent moiety may comprise a dioxo-pyridine ring (DPR) or a thiazolopyridine acid (TPA).

In some embodiments, the method of imaging a biological environment may be a dual-imaging method that, in addition to the disposing step, comprises the following steps: (1) exposing the biological environment to radio-frequency electromagnetic radiation while the biological environment is disposed in a magnetic field, thereby exciting hydrogen atoms of the biological environment, and then detecting relaxation of the excited hydrogen atoms; and (2) exposing the biological environment to electromagnetic radiation having a wavelength corresponding to an excitation wavelength of a photoluminescent moiety of the polymer or oligomer, and then detecting light emitted by the luminescent moiety. These additional steps may be performed in any order. In these dual-imaging embodiments, the disposed composition is an MRI-sensitive and photoluminescent composition, which may comprise citrate-containing polymers or oligomers as described herein that are photoluminescent or both MRI-sensitive and photoluminescent. The luminescent moiety may comprise a dioxo-pyridine ring (DPR) or a thiazolopyridine acid (TPA).

In a further aspect, a graft or scaffold comprising any of the compositions described herein is described. When used to form a graft or scaffold, the compositions described herein may be cross-linked to form a polymer network and a particulate inorganic material may be dispersed in the polymer network. In some embodiments, the particulate inorganic material comprises one or more of hydroxyapatite, tricalcium phosphate, biphasic calcium phosphate, bioglass, ceramic, magnesium powder, magnesium alloy, and decellularized bone tissue particles. In certain cases, the graft or scaffold further comprises a porous shell component and/or a porous core component. For example, in some embodiments, the graft or scaffold comprises a porous shell component surrounding a porous core component. In some such instances, the core component and the shell component are concentric cylinders.

These and other embodiments are described in more detail in the detailed description that follows.

DETAILED DESCRIPTION

Figure 1:
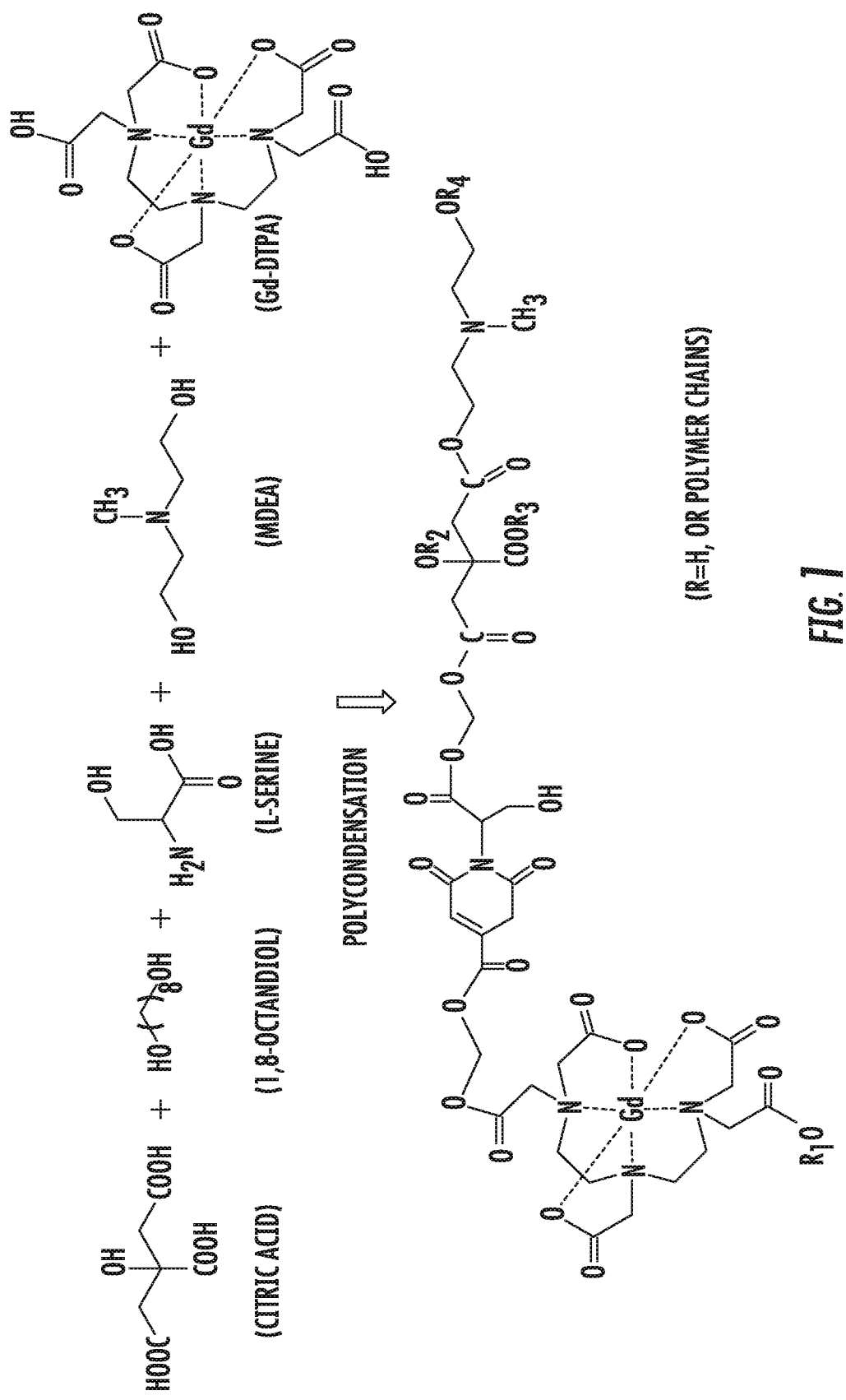
FIG. 1 is a schematic synthesis of a fluorescent and MRI dual-imaging polymer BPLPMGd as disclosed herein.

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9. Similarly, a stated range of "1 to 10" should be considered to include any and all subranges beginning with a minimum value of 1 or more and ending with a maximum value of 10 or less, e.g., 1 to 5, or 4 to 10, or 3 to 7, or 5 to 8.

All ranges disclosed herein are also to be considered to include the end points of the range, unless expressly stated otherwise. For example, a range of "between 5 and 10," or "from 5 to 10," or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. MRI-Active or Sensitive Compositions

In one aspect, MRI-sensitive compositions are described herein. The term MRI-active or MRI-sensitive means that the compositions comprise, consist of, or consist essentially of one or more MRI contrast agents. MRI contrast agents, as understood by one of ordinary skill in the art, are compounds, complexes, or other species that improve the visibility of internal body structures in magnetic resonance imaging (MRI).

In some embodiments, the MRI-sensitive compositions described herein comprise, consist of, or consist essentially of one or more polymers or oligomers that are MRI-sensitive. In some embodiments, the MRI-sensitive polymers or oligomers may be citrate-containing polymers or oligomers. In some embodiments, the one or more MRI-sensitive citrate-containing polymers or oligomers have an MRI-contrast agent integrated into or pendant from their polymeric or oligomeric backbone. For example, the one or more MRI-sensitive citrate-containing polymers or oligomers may be formed by reacting one or more monomers that comprise an MRI contrast agent. The polymers or oligomers have an MRI contrast agent moiety.

The MRI contrast agent is not so limited, and any MRI contrast that is not inconsistent with the objectives of the present disclosure may be used in an MRI-sensitive composition as disclosed herein. For example, non-limiting examples of MRI contrast agents are disclosed in the following publications: Rashid, H. Ur., et al. "Lanthanide(III) Chelates as MRI Contrast Agents: Brief Description," *J. Structural Chem.*, Vol. 54, No. 1, pp. 223-249, 2013; Laurent, S. et al. (2017). *MRI Contrast Agents: From Molecules to Particles*, Springer e-book; Frullano, L. et al., "Multimodal MRI Contrast Agents," *J. Biol. Inorg. Chem.*, (2007) 12:939-949; Tang, J., et al., "Macromolecular MRI Contrast Agents: Structures, Properties, and Applications," *Progress in Polymer Sci.*, 38 (2013) 462-502. Each of these publications is incorporated herein by reference.

In some embodiments, the MRI contrast agent comprises a lanthanide metal ion. In some embodiments, the lanthanide metal is Gd. Other lanthanide metal ions may also be used, such as Nd, Sm, Eu, Tb, Dy, Ho, or Er. Moreover, the lanthanide metal ion can be in the +2 or the +3 oxidation state, such as in $Gd^{3+}$. Some examples of MRI contrast agents are shown in FIGS. 12-16. It should be noted, with reference to FIGS. 12-16, that the lanthanide ion (e.g., $Gd^{3+}$) is not shown in each structure. Such structures can be considered to be "ligands" for MRI contrast agents. Moreover, it is to be understood that a lanthanide ion can be present (and generally is present) in an MRI contrast agent corresponding to such a structure or ligand.

In some embodiments, the MRI contrast agent comprises a metal coordination compound, metal complex, or molecular metal-ligand complex. In some embodiments, the MRI contrast agent comprising a metal coordination compound, metal complex, or molecular metal-ligand complex has the structure of Formula (J1) or (J2):

$$HO-[M]-OH \quad (J1), \text{ and}$$

$$HOOC-[M]-COOH \quad (J2),$$

wherein [M] represents a metal-containing (e.g., lanthanide ion-containing) portion of the MRI contrast agent. In some instances, the portion [M] may include or consist of the metal itself and the immediate coordination or ligand environment of the metal. For example, in some preferred embodiments, the MRI contrast agent comprises gadolinium-diethylenetriamine pentaacetic acid (Gd-DTPA). Alternatively, in other cases, an MRI contrast agent described herein includes a metal-containing portion [M] coupled or attached to, or otherwise including, one or more moieties other than a hydroxyl or carboxyl moiety. Combinations of differing moieties are also possible. For instance, in some embodiments, an MRI contrast agent described herein has the structure of Formula (J3), (J4), (J5), or (J6):

$$H_2N-[M]-NH_2 \quad (J3),$$

$$HO-[M]-COOH \quad (J4),$$

$$HO-[M]-NH_2 \quad (J5), \text{ and}$$

$$HOOC-[M]-NH_2 \quad (J6).$$

As understood by one of ordinary skill in the art, MRI contrast agents having a structure described above can participate in a chemical reaction between a nucleophile and an electrophile, such as may occur in a condensation polymerization reaction described herein. For example, in some cases, the more electronegative atom of the amine, hydroxyl, and/or carboxyl moieties of an MRI contrast agent described above can act as a nucleophile in a polycondensation reaction with a polycarboxylic acid (or equivalent species), such as a citrate-containing monomer described herein. In this manner, the metal-containing portion [M] of an MRI contrast agent described herein can be incorporated into the backbone of a polymer or oligomer described herein.

It is further to be understood that an MRI contrast agent described above (such as a commercially available MRI contrast agent), in some cases, can be altered to have the structure of Formula (J1), (J2), (J3), (J4), (J5), or (J6), if needed or desired. For example, an MRI contrast agent that does not include two or more $NH_2$, OH, or COOH moieties can be chemically altered to include such moieties, using standard chemical reactions known to one of ordinary skill in the art.

Additionally, in some preferred embodiments, the MRI contrast agent is a lanthanide-containing complex in which the lanthanide metal remains in the complex after incorporation of the complex into a polymer or oligomer in a manner described herein. For example, the lanthanide metal can remain complexed even after the polymer or oligomer is formed by reacting a monomer comprising the MRI contrast agent with other monomers described herein. Moreover, in some especially preferred embodiments, the MRI contrast agent is incorporated into a polymer or oligomer through OH and/or COOH moieties, but not by $NH_2$ moieties or other moieties that form reaction products with a carboxylic acid that are not readily biodegradable or are not as biodegradable as ester linkages. Using OH and COOH moieties can thus improve or maintain the biodegradability of the overall polymer or oligomer containing the MRI contrast agent.

Any citrate-containing polymer not inconsistent with the objectives of the present disclosure may be used in an MRI-sensitive composition as disclosed herein. A "citrate-containing polymer or oligomer" for reference purposes herein, comprises, consists of, or consists essentially of a polymer or oligomer formed from one or more monomers including citric acid, citrate, or an ester or amide of citric acid. The one or more monomers may have a structure of Formula (A1):

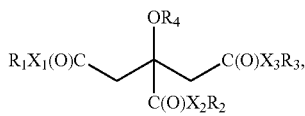
(A1)

wherein $X_1$, $X_2$, and $X_3$, are each independently —O— or —NH—;

$R_1$, $R_2$, and $R_3$ are each independently —H, a C1 to C22 alkyl or alkenyl group, or $M^+$;

$R_4$ is —H, a C1 to C22 alkyl or alkenyl group, or $M^+$; and $M^+$ is a monovalent metal cation such as $Na^+$ or $K^+$, or a divalent metal cation such as $Ca^{2+}$ or $Mg^{2+}$.

Further, it is to be understood that a "C1 to Cn" alkyl or alkenyl group refers to an alkyl or alkenyl group having 1 to n carbon atoms. The alkyl or alkenyl group may have 1, 2, 3, 4, 5, 6, 7, 8, 9, 10, 11, 12, 13, 14, 15, 16, 17, 18, 19, 21, 21, 22, or n carbon atoms. Additionally, when the foregoing monomer is incorporated into the polymer or oligomer, at least one of $R_1$, $R_2$, and $R_3$ is a point of attachment to the remainder of the polymer or oligomer.

The monomer of Formula (A1) may be referred to as a non-alkoxylated and non-alkenoxylated citric acid, citrate, or ester/amide of citric acid. In some embodiments, the monomer of Formula (A1) also may be reacted with a monomer of Formula (A2), which may be referred to as an alkoxylated or alkenoxylated citric acid, citrate, or ester amide of citric acid, to form the polymer or oligomer of the compositions described herein. Formula (A2) is the following:

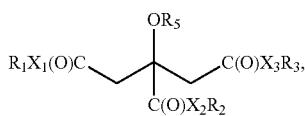
(A2)

wherein $X_1$, $X_2$, and $X_3$, are each independently —O— or —NH—;

$R_1$, $R_2$, and $R_3$ are each independently —H, a C1 to C22 alkyl or alkenyl group, or $M^+$;

$R_5$ is $C(O)R_{23}$;

$R_{23}$ is a C14 to C22 alkyl or alkenyl group; and $M^+$ is a monovalent metal cation such as $Na^+$ or $K^+$, or a divalent metal cation such as $Ca^{2+}$ or $Mg^{2+}$. Reaction of (A2) to form the polymer or oligomer of the compositions described herein is optional. For example, (A2) may be reacted if a polymer or oligomer with antibacterial or antifungal properties is desired. When the monomer (A2) is incorporated into the polymer as an alkoxylated or alkenoxylated citrate moiety, at least one of $R_1$, $R_2$, and $R_3$ is a point of attachment to the remainder of the polymer. It is to be understood that, as denoted in Formula (A2) and as described further herein below, an alkyl or alkenyl moiety can be included in the $R_5$ position through alkoxylation or alkenoxylation of a citric acid, citrate, or citric acid ester or amide. Not intending to be bound by theory, it is believed that fatty acids with alkyl or alkenyl moieties such as described herein may exhibit antifungal properties due to their ability to insert into and disrupt the lipid bilayer of the fungus.

In some cases, an MRI-sensitive polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent. In other cases, an MRI-sensitive polymer or oligomer of a composition described herein comprises the reaction product of (i) a non-alkoxylated and non-alkenoxylated citric acid, citrate, or ester/amide of citric acid, e.g., a monomer of Formula (A1) and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, and (iv) an amino acid.

Non-limiting examples of polyols/polyamines suitable for use in some embodiments described herein include C2-C20, C2-C12, or C2-C6 aliphatic alkane diols/diamines, including α,ω-n-alkane diols/diamines, or α,ω-alkene diols/diamines. For instance, in some cases, a polyol/polyamine comprises 1,4-butanediol/diamine, 1,6-hexanediol/diamine, 1,8-octanediol/diamine, 1,10-decanediol/diamine, 1,12-dodecanediol/diamine, 1,16-hexadecanediol/diamine, or 1,20-icosanediol/diamine. Branched α,ω-alkane diols/diamines or α,ω-alkene diols/diamines can also be used. Additionally, a polyol/polyamine can also be an aromatic diol/diamine. Further, in some embodiments, a polyol/polyamine comprises a poly(ethylene glycol) (PEG) or poly(propylene glycol) (PPG) having terminal hydroxyl or amine groups. Any such PEG or PPG not inconsistent with the objectives of the present disclosure may be used. In some embodiments, for instance, a PEG or PPG has a weight average molecular weight between about 100 and about 5000 or between about 200 and about 1000.

In some embodiments, the polyol/polyamine may have the structures represented by Formula (B1) and/or Formula (B2):

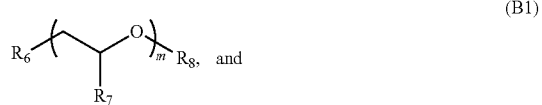
(B1)

(B2)

wherein $R_6$ is —H, —$NH_2$, —OH, —$OCH_3$, —$OCH_2CH_3$, —$CH_3$, or —$CH_2CH_3$;

$R_7$ is —H or a C1 to C22 alkyl or alkenyl group such as —$CH_3$;

$R_8$ is —H; a C3 to C22 alkyl or alkenyl group such as —$CH_3$ or —$CH_2CH_3$; —$CH_2CH_2OH$; or —$CH_2CH_2NH_2$; and n and m are independently integers ranging from 1 to 100 or 1 to 20.

Further, the monomers of Formula (A1), optional (A2), (B1), and (B2) can be used in any ratio not inconsistent with the objectives of the present disclosure. In addition, altering the ratios of monomers can, in some embodiments, alter the antimicrobial properties, the MRI-activity, the biodegradability, the mechanical strength, and/or other properties of the polymer formed from the monomers. In some embodiments, the ratio of monomer (A1) to monomer (B1), or monomer (B2) is between about 1:10 and about 10:1 or between about 1:5 and about 5:1. In some embodiments, the ratio of monomer (A1) to monomer (B1), or monomer (B2) is between about 1:4 and about 4:1. In some embodiments, the ratio is about 1:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1. Additionally, when (A2) is reacted, the ratio of monomer (A2) to monomer (B1), or monomer (B2) in some instances, is between about 1:10 and about 10:1 or between about 1:5 and about 5:1. In some embodiments, the ratio of monomer (A2) to monomer (B1), or monomer (B2) is between about 1:4 and about 4:1. In some embodiments, the ratio is about 1:1.

Non-limiting examples of MRI contrast agents suitable for use as monomers are described hereinabove. In some cases, as described above, the monomers comprising an MRI contrast agent may comprise, consist of, or consist essentially of an MRI contrast agent (e.g., an MRI contrast agent having the structure of Formula (J1) or Formula (J2)). Additionally, as understood by one of ordinary skill in the art, a monomer for a polymerization reaction described herein generally comprises at least one reactive or polymerizable functional group or moiety. Thus, in some embodiments, known MRI contrast agents may need to be modified so that they are monomers for purposes of a polymerization reaction described herein. For example, as described above, a known MRI contrast agent can be modified by known methods to include two or more hydroxyl or carboxyl groups.

Moreover, the monomers of Formula (A1), optional (A2), (B1), (B2), and the monomer comprising the MRI contrast agent can be used in any ratio not inconsistent with the objectives of the present disclosure. In some embodiments, the ratio of monomer (A1) or monomer (A2), if reacted, to monomer (B1), monomer (B2), or the monomer comprising the MRI contrast agent is between about 1:10 and about 10:1 or between about 1:5 and about 5:1. In some embodiments, the ratio of monomer (A1) or monomer (A2), if reacted, to monomer (B1), monomer (B2), or the monomer comprising the MRI contrast agent is between about 1:4 and about 4:1. In some cases, the ratio is about 1:1. Further, in some embodiments, the ratio of monomer (A1), monomer (A2), monomer (B1), or monomer (B2) to the monomer comprising an MRI contrast agent is between about 1:10 and about 10:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1.

Non-limiting examples of amino acids suitable for use in some embodiments described herein include alpha amino acids. An alpha-amino acid of a polymer described herein, in some embodiments, comprises an L-amino acid, a D-amino acid, or a D,L-amino acid. In some cases, an alpha-amino acid comprises alanine, arginine, asparagine, aspartic acid, cysteine, glycine, glutamine, glutamic acid, histidine, isoleucine, leucine, lysine, methionine, proline, phenylalanine, serine, threonine, tyrosine, tryptophan, valine, or a combination thereof. Further, in some instances, an alpha-amino acid comprises an alkyl-substituted alpha-amino acid, such as a methyl-substituted amino acid derived from any of the 22 "standard" or proteinogenic amino acids, such as methyl serine. An amino acid monomer may one of Formula (F):

wherein $R_{15}$ is an amino acid side chain.

Moreover, the monomers of Formula (A1), optional (A2), (B1), (B2), the monomer comprising the MRI contrast agent, and monomer (F) can be used in any ratio not inconsistent with the objectives of the present disclosure. In some embodiments, the ratio of monomer (A1) or monomer (A2), if reacted, to monomer (B1), monomer (B2), the monomer comprising the MRI contrast agent, or monomer (F) is between about 1:10 and about 10:1 or between about 1:5 and about 5:1. In some embodiments, the ratio of monomer (A1) or monomer (A2), if reacted, to monomer (B1), monomer (B2), the monomer comprising the MRI contrast agent, or monomer (F) is between about 1:4 and about 4:1. In some cases, the ratio is about 1:1. Further, in some embodiments, the ratio of monomer (A1), monomer (A2), monomer (B1), monomer (B2), or the monomer comprising the MRI contrast agent to monomer (F) is between about 1:10 and about 10:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1.

A reaction product described hereinabove, in some cases, is a condensation polymerization reaction product of the identified species (A1), optional (A2), (B1) or (B2), (F), and a monomer comprising an MRI contrast agent. Thus, in some embodiments, at least two of the identified species are comonomers for the formation of a copolymer. In some such embodiments, the reaction product forms an alternating copolymer or a statistical copolymer of the comonomers. Additionally, species described hereinabove may also form pendant groups or side chains of a copolymer, or may form cyclic structures that may form part of the backbone of the polymer. Moreover, in some cases, the amount or ratio of a comonomer or other reactant comprising an alkoxylated or alkenoxylated citrate moiety can be selected to provide a desired antimicrobial effect to the alkoxylated or alkenoxylated citrate-containing polymer. Surprisingly, it has been discovered that some antimicrobial properties of a composition described herein, e.g., the compositions where monomer (A2) or an alkoxylated or alkenoxylated citric acid, citrate, or ester/amide of citric acid is reacted, can be tuned by varying one or more of the mole percent or weight percent of an alkoxylated or alkenoxylated citrate moiety in an MRI active citrate-containing polymers, the biodegradability of an MRI-sensitive citrate-containing polymer, and the water swellability of an MRI active citrate-containing polymer. In some cases, an MRI active polymer or oligomer described herein comprises at least about 30 mole percent, at least about 40 mole percent, or at least about 50 mole percent citrate moiety, based on the total number of moles of the comonomers of the polymer. In some embodiments, an MRI active polymer or oligomer described herein comprises between about 30 mole percent and about 70 mole percent, between about 30 mole percent and about 60 mole percent, between about 30 mole percent and about 50 mole percent, between about 35 mole percent and about 60 mole percent, between about 35 mole percent and about 55 mole percent, between about 40 mole percent and about 70 mole percent, between about 40 mole percent and about 60 mole percent, or between about 40 mole percent and about 55 mole percent alkoxylated or alkenoxylated citrate moiety, based on the total number of moles of the comonomers of the polymer. Similarly, in some cases, an MRI active polymer or oligomer described herein comprises at least about 5 weight percent, at least about 10 weight percent, or at least about 15 weight percent, at least about 25 weight percent, at least about 30 weight percent, or at least about 40 weight percent alkoxylated or alkenoxylated citrate moiety, based on the total weight of the polymer. In some embodiments, an MRI active polymer or oligomer described herein comprises between about 5 weight percent and about 80 weight percent, between about 5 weight percent and about 70 weight percent, between about 10 weight percent and about 80 weight percent, between about 10 weight percent and about 60 weight percent, between about 20 weight percent and about 80 weight percent, between about 20 weight percent and about 60 weight percent, between about 30 weight percent and about 80 weight percent, or between about 40 weight percent and about 70 weight percent alkoxylated or alkenoxylated citrate moiety, based on the total weight of the polymer.

In some embodiments, an MRI active polymer or oligomer described herein comprises between about 30 mole percent and about 70 mole percent, between about 30 mole percent and about 60 mole percent, between about 30 mole percent and about 50 mole percent, between about 35 mole percent and about 60 mole percent, between about 35 mole percent and about 55 mole percent, between about 40 mole percent and about 70 mole percent, between about 40 mole percent and about 60 mole percent, or between about 40 mole percent and about 55 mole percent MRI contrast agent moiety, based on the total number of moles of the comonomers of the polymer. Similarly, in some cases, an MRI active polymer or oligomer described herein comprises at least about 5 weight percent, at least about 10 weight percent, or at least about 15 weight percent, at least about 25 weight percent, at least about 30 weight percent, or at least about 40 weight percent MRI contrast agent moiety, based on the total weight of the polymer. In some embodiments, an MRI active polymer or oligomer described herein comprises between about 5 weight percent and about 80 weight percent, between about 5 weight percent and about 70 weight percent, between about 10 weight percent and about 80 weight percent, between about 10 weight percent and about 60 weight percent, between about 20 weight percent and about 80 weight percent, between about 20 weight percent and about 60 weight percent, between about 30 weight percent and about 80 weight percent, or between about 40 weight percent and about 70 weight percent MRI contrast agent moiety, based on the total weight of the polymer.

In general, an MRI active polymer described herein can be an MRI-sensitive derivative of a polymer or oligomer described in U.S. Pat. Nos. 7,923,486; 8,530,611; 8,574,311; 8,613,944; U.S. Patent Application Publication No. 2012/0322155; U.S. Patent Application Publication No. 2013/0217790; or U.S. Patent Application Publication No. 2014/066587; the entireties of which are hereby incorporated by reference. For example, in some cases, an MRI-sensitive citrate-containing polymer of a composition described herein comprises an MRI-sensitive poly(ethylene glycol maleate citrate) (PEGMC), poly(octamethylene citrate) (POC), poly(octamethylene maleate anhydride citrate) (POMC), or a crosslinkable urethane doped elastomer (CUPE) or biodegradable photoluminescent polymer (BPLP). As described above, it is to be understood that an MRI active derivative of a polymer or oligomer described above can be a variation of the polymer or oligomer above in and MRI contrast agent is incorporated into or pendant from the polymer or oligomer. An MRI active derivative of a polymer or oligomer described above is understood to be a polymer or oligomer as described above that is also formed from a monomer comprising an MRI contrast agent. In other words, an MRI contrast agent comprising monomer is also reacted when forming the polymers.

Further, one or more other properties of an MRI active polymer described herein may also be tuned based on the amount of the optional alkoxylated or alkenoxylated citrate moiety, the amount of MRI contrast agent moiety and/or on one or more other features of the chemical structure of the polymer. For example, in some cases, the water uptake and/or degradation rate of a polymer described herein can be tuned for a desired application. Such tunability can provide further advantages to a composition described herein. For example, as described above, some previous biodegradable polymers and gels require incorporation of antibiotics or inorganic materials like silver nanoparticles to exhibit antimicrobial properties. Thus, a high swelling ratio of such polymers could lead to a "burst" release rather than a sustained release of bacteria-killing and/or fungi-killing agents, thereby limiting the anti-infection applications of such compositions. In contrast, some MRI-sensitive citrate-containing polymers and compositions described herein can have decoupled swelling and antimicrobial properties. Therefore, the structure and chemical composition of some MRI active citrate-containing polymers and compositions described herein can be selected to satisfy other requirements, such as mechanical requirements, without the need to sacrifice antimicrobial performance, including long term antimicrobial performance.

Additionally, an MRI-sensitive citrate-containing polymer described herein can have at least one ester bond in the backbone of the polymer. In some cases, a polymer has a plurality of ester bonds in the backbone of the polymer, such as at least three ester bonds, at least four ester bonds, or at least five ester bonds. In some embodiments, a polymer described herein has between two ester bonds and fifty ester bonds in the backbone of the polymer. Polymers having one or more ester bonds in the backbone of the polymer can be hydrolyzed in a biological or other aqueous environment to release free citric acid or citrate, in addition to other components. Not intending to be bound by theory, it is believed that the presence of citric acid in a biological environment can contribute to pH reduction, which may depress the internal pH of bacteria and alter the permeability of the bacterial membrane by disrupting substrate transport.

Further, MRI active citrate-containing polymers having a structure described herein, in some cases, can be biodegradable. A biodegradable polymer, in some embodiments, degrades in vivo to non-toxic components which can be cleared from the body by ordinary biological processes. In some embodiments, a biodegradable polymer completely or substantially completely degrades in vivo over the course of about 90 days or less, about 60 days or less, or about 30 days or less, where the extent of degradation is based on percent mass loss of the biodegradable polymer, and wherein complete degradation corresponds to 100% mass loss. Specifically, the mass loss is calculated by comparing the initial weight ($W_0$) of the polymer with the weight measured at a pre-determined time point ($W_t$) (such as 30 days), as shown in equation (1):

$$\text{Mass Loss}(\%) = \frac{(w_o - w_t)}{w_o} \times 100. \quad (1)$$

In some cases, a polymer or oligomer having surprisingly strong underwater adhesive properties is formed from one or more monomers of Formula (A1), optionally one or more monomers of Formula (A2), one or more monomers of Formula (B1) or (B2), one or more monomers (F), one or more monomers comprising an MRI contrast agent, and dopamine. In other cases, the polymer or oligomer having surprisingly strong underwater adhesive properties is formed from one or more monomers of Formula (A1), optionally one or more monomers of Formula (A2), one or more monomers of Formula (B1) or (B2), one or more monomers of Formula (F), one or more monomers comprising an MRI contrast agent, L-DOPA, D-DOPA or gallic acid, and caffeic acid, 3,4-dihydroxyhydrocinnamic acid, or tannic acid.

In some cases, an MRI-sensitive polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, (iii) a monomer comprising an MRI contrast agent, and (v) an amine-containing diol. In other cases, a polymer or oligomer of a composition described herein comprises the reaction product of (i) a non-alkoxylated and non-alkenoxylated citric acid, citrate, or ester/amide of citric acid, e.g., a monomer of Formula (A1) and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, and (v) an amine-containing diol.

The amine-containing diol can comprise any amine-containing diol not inconsistent with the objectives of the present disclosure. For example, the amine-containing diol may have a structure of Formula (K):

(K)

wherein $R_{24}$ is —H or a C1 to C20 alkyl or alkenyl group; and r and s are each independently an integer between 0 and 20, 1 and 20, 2 and 20, 3 and 20, 5 and 20, 10 and 20, or 15 and 20. In one preferred embodiment, $R_{24}$ is —CH$_3$ and r and s are both 2. In this case, the amine-containing diol is methyl diethyl amine (MDEA). In other embodiments, the amine-containing diol may be methyl dipropyl amine, methyl dibutyl amine, or methyl dipentyl amine. Without wishing to be bound by any particular theory, it is believed that forming the polymer or oligomer from an amine-containing diol, particularly MDEA, increases the mechanical strength of the polymer or oligomer, particularly when the polymer or oligomer is used to form a graft or scaffold for tissue engineering applications. It increases the mechanical strength, while maintaining other desirable characteristics such as degradability and/or biodegradability.

Moreover, the monomers of Formula (A1), optional (A2), (B1), (B2), (F), (K), and the monomer comprising the MRI contrast agent can be used in any ratio not inconsistent with the objectives of the present disclosure. In some embodiments, the ratio of monomer (A1) or monomer (A2), if reacted, to monomer (B1), monomer (B2), the monomer comprising the MRI contrast agent, monomer (F), and monomer (K) is between about 1:10 and about 10:1 or between about 1:5 and about 5:1. In some embodiments, the ratio is between about 1:4 and about 4:1. In some cases, the ratio is about 1:1. Further, in some embodiments, the ratio of monomer (A1), monomer (A2), monomer (B1), monomer (B2), the monomer comprising the MRI contrast agent, or the monomer (F) to monomer (K) is between about 1:10 and about 10:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1.

In some cases, an MRI-sensitive polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, (iii) a monomer comprising an MRI contrast agent, and (vi) a catechol-containing species. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, and (vi) a catechol containing species. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) an amine-containing diol, and (vi) a catechol containing species.

The catechol-containing species can comprise any catechol-containing species not inconsistent with the objectives of the present disclosure. In some cases, a catechol-containing species used to form an MRI-sensitive polymer or oligomer described herein comprises at least one moiety that can form an ester or amide bond with another chemical species used to form the polymer. For example, in some cases, a catechol-containing species comprises an alcohol moiety, an amine moiety, a carboxylic acid moiety, or a combination thereof. Further, in some instances, a catechol-containing species comprises a hydroxyl moiety that is not part of the catechol moiety. In some embodiments, a catechol-containing species comprises dopamine. In other embodiments, a catechol-containing species comprises L-3,4-dihydroxyphenylalanine (L-DOPA) or D-3,4-dihydroxyphenylalanine (D-DOPA). In still other embodiments, a catechol-containing species comprises gallic acid or caffeic acid. In some cases, a catechol-containing species comprises 3,4-dihydroxyhydrocinnamic acid. Additionally, a catechol-containing species may also comprise a naturally-occurring species or a derivative thereof, such as tannic acid or a tannin. Moreover, in some embodiments, a catechol-containing species is coupled to the backbone of the polymer through an amide bond. In other embodiments, a catechol-containing species is coupled to the backbone of the polymer through an ester bond. In some embodiments, the catechol-containing species may be represented by Formula (C):

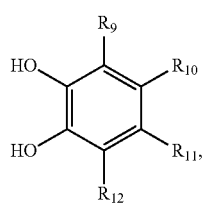

(C)

wherein $R_9$, $R_{10}$, $R_{11}$, and $R_{12}$ are each independently —H, —OH, —CH$_2$(CH$_2$)$_x$NH$_2$, —CH$_2$(CHR$_{13}$)NH$_2$, —CH$_2$(CH$_2$)$_x$OH, —CH$_2$(CHR$_{13}$)OH, —CH$_2$(CH$_2$)$_x$COOH, or a point of attachment to a polymer chain;

$R_{13}$ is —COOH or —(CH$_2$)$_y$COOH;

x is an integer ranging from 0 to 10; and y is an integer ranging from 1 to 10.

In some cases, a monomer of Formula (C) comprises dopamine, L-DOPA, D-DOPA, gallic acid, caffeic acid, 3,4-dihydroxyhydrocinnamic acid, or tannic acid. Moreover, in some embodiments, a monomer of Formula (C) is coupled to the backbone of the polymer or oligomer described herein through an amide bond. In other embodiments, a monomer of Formula (C) is coupled to the backbone of the polymer through an ester bond.

Moreover, the monomers of Formula (A1), optional (A2), (B1), (B2), (F), (C), and the monomer comprising an MRI contrast agent can be used in any ratio not inconsistent with the objectives of the present disclosure. In addition, altering the ratios of monomers can, in some embodiments, alter the antimicrobial or MRI-activity properties and/or other properties of the MRI-sensitive citrate-containing polymer or oligomers formed from the monomers. In some embodiments, the ratio of monomer (A1) or monomer (A2) to monomer (B1), monomer (B2), monomer (C), monomer (F), or the monomer comprising the MRI contrast agent is between about 1:10 and about 10:1 or between about 1:5 and about 5:1. In some embodiments, the ratio is between about 1:4 and about 4:1. In some cases, the ratio is about 1:1. Further, in some embodiments, the ratio of monomer (A1), monomer (A2), monomer (B1), monomer (B2), monomer (F), or the monomer comprising the MRI contrast agent to monomer (C) is between about 1:10 and about 10:1. Further, in some embodiments, the ratio of monomer (A1) to monomer (A2) is between about 1:10 and about 10:1. In some embodiments it is 1:1.

An MRI-sensitive citrate-containing polymer or oligomer of a composition described herein, in some cases, can comprise the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, (iii) a monomer comprising an MRI contrast agent, and (vii) an isocyanate. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, and (vii) an isocyanante. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) an amine-containing diol and (vii) an isocyanante. In other cases, a polymer or oligomer of a composition described herein comprises the reaction product of (i) a non-alkoxylated and non-alkenoxylated citric acid, citrate, or ester/amide of citric acid, e.g., a monomer of Formula (A1) and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) an amine-containing diol, (vi) a catechol-containing species, and (vii) an isocyanante. An isocyanate, in some embodiments, comprises a monoisocyanate. In other instances, an isocyanate comprises a diisocyanate such as an alkane diisocyanate having four to twenty carbon atoms. An isocyanate described herein may also include a monocarboxylic acid moiety.

In some embodiments, the isocyanate may be represented by Formula (D1), Formula (D2), Formula (D3), and/or Formula (D4):

(D1)

(D2)

(D3)

(D4)

wherein p is an integer ranging from 1 to 10.

Moreover, the monomers of Formula (A1), optional (A2), (B1), (B2), (F), (D1), (D2), (D3), (D4), and the monomer comprising an MRI contrast agent can be used in any ratio not inconsistent with the objectives of the present disclosure. In addition, altering the ratios of monomers can, in some embodiments, alter the antimicrobial or MRI-activity properties and/or other properties of the MRI-sensitive citrate-containing polymer or oligomers formed from the monomers. In some embodiments, the ratio of monomer (A1) or monomer (A2) to monomer (B1), monomer (B2), monomer (C), monomer (F), monomer (D1), monomer (D2), monomer (D3), monomer (D4), or the monomer comprising the MRI contrast agent is between about 1:10 and about 10:1 or between about 1:5 and about 5:1. In some embodiments, the ratio is between about 1:4 and about 4:1. In some cases, the ratio is about 1:1. Further, in some embodiments, the ratio of monomer (A1), monomer (A2), monomer (B1), monomer (B2), monomer (F), or the monomer comprising the MRI contrast agent to the monomer (D1), (D2), (D3), or (D4) is between about 1:10 and about 10:1. Further, in some embodiments, the ratio of monomer (A1) to monomer (A2) is between about 1:10 and about 10:1. In some embodiments it is 1:1.

In addition, an MRI-sensitive citrate-containing polymer of a composition described herein can also comprise the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, (iii) a monomer comprising an MRI contrast agent, and (viii) a polycarboxylic acid such as a dicarboxylic acid or a functional equivalent of a polycarboxylic acid, such as a cyclic anhydride or an acid chloride of a polycarboxylic acid. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, and (viii) a polycarboxylic acid such as a dicarboxylic acid or a functional equivalent of a polycarboxylic acid, such as a cyclic anhydride or an acid chloride of a polycarboxylic acid. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) an amine-containing diol and (viii) a polycarboxylic acid such as a dicarboxylic acid or a functional equivalent of a polycarboxylic acid, such as a cyclic anhydride or an acid chloride of a polycarboxylic acid. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) a an amine-containing diol, (vi) a catechol-containing species, and (viii) a polycarboxylic acid such as a dicarboxylic acid or a functional equivalent of a polycarboxylic acid, such as a cyclic anhydride or an acid chloride of a polycarboxylic acid. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) a an amine-containing diol, (vi) a catechol-containing species, (vii) an isocyanate, and (viii) a polycarboxylic acid such as a dicarboxylic acid or a functional equivalent of a polycarboxylic acid, such as a cyclic anhydride or an acid chloride of a polycarboxylic acid. Moreover, the polycarboxylic acid or functional equivalent thereof can be saturated or unsaturated. For example, in some instances, the polycarboxylic acid or functional equivalent thereof comprises maleic acid, maleic anhydride, fumaric acid, or fumaryl chloride. A vinyl-containing polycarboxylic acid or functional equivalent thereof may also be used, such as allylmalonic acid, allylmalonic chloride, itaconic acid, or itaconic chloride. Further, in some cases, the polycarboxylic acid or functional equivalent thereof can be at least partially replaced with an olefin-containing monomer that may or may not be a polycarboxylic acid. In some embodiments, for instance, an olefin-containing monomer comprises an unsaturated polyol such as a vinyl-containing diol.

In some embodiments, the polycarboxylic acid may be represented by Formula (E1) and/or Formula (E2):

$$R_{14}(O)C\diagdown\diagup C(O)R_{14} \quad \text{and} \tag{E1}$$

$$\underset{O}{\diagdown}\underset{O}{\diagup}\underset{O}{\diagdown}O, \tag{E2}$$

wherein $R_{14}$ is OH, $OCH_3$, $OCH_2CH_3$, or Cl.

Further, the monomers of Formula (A1), optional (A2), (B1), (B2), (F), (E1), (E2), and the monomer comprising the MRI contrast agent can be used in any ratio not inconsistent with the objectives of the present disclosure. In addition, altering the ratios of monomers can, in some embodiments, alter the MRI activity, the antimicrobial properties, the biodegradability, the mechanical strength, and/or other properties of the polymer formed from the monomers. In some embodiments, the ratio of monomer (A1) or monomer (A2) to monomer (B1), monomer (B2), monomer (F), monomer (E1), or monomer (E2) is between about 1:10 and about 10:1 or between about 1:5 and about 5:1. In some embodiments, the ratio is between about 1:4 and about 4:1. In some embodiments, the ratio is about 1:1. Further, in some embodiments, the ratio of the monomer comprising the MRI contrast agent to monomer (E1) or monomer (E2) is between about 1:10 and about 10:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1.

In some instances an MRI-sensitive citrate-containing polymer of a composition described herein can also comprise the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, (iii) a monomer comprising an MRI contrast agent, and (ix) a diamine. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, and (ix) a diamine. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) a an amine-containing diol, and (ix) diamine. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) a an amine-containing diol, (vi) a catechol-containing species, and (ix) a diamine. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) an amine-containing diol, (vi) a catechol-containing species, (vii) an isocyanate, and (ix) a diamine. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) an amine-containing diol, (vi) a catechol-containing species, (vii) an isocyanate, (viii) a polycarboxylic acid, and (ix) a diamine.

In some embodiments, the diamine may be represented by the structure of Formula (G):

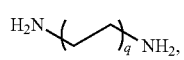

(G)

wherein q is an integer ranging from 1 to 20, 1 to 15, 1 to 10, or 1 to 5.

In some cases, the diamine may at least partially replace a diol monomer such as Formula (B1) or Formula (B2) described hereinabove. In other cases, the diamine may be used in addition to diol monomers and/or instead of the diol monomers. Not intending to be bound by theory, the use of diamine will result in amide linkages in the polymer or oligomer, which may in turn result in slower degradation of the polymer or oligomer, giving a means to "tune" the degradability of the polymer or oligomer.

In some instances an MRI-sensitive citrate-containing polymer of a composition described herein can also comprise the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, (iii) a monomer comprising an MRI contrast agent, and (x) one or more monomers comprising one or more alkyne moieties and/or one or more azide moieties. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, and (x) one or more monomers comprising one or more alkyne moieties or one or more azide moieties. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) a an amine-containing diol, and (x) one or more monomers comprising one or more alkyne moieties or one or more azide moieties. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) a an amine-containing diol, (vi) a catechol-containing species, and (x) one or more monomers comprising one or more alkyne moieties or one or more azide moieties. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) an amine-containing diol, (vi) a catechol-containing species, (vii) an isocyanate, and (x) one or more monomers comprising one or more alkyne moieties or one or more azide moieties. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) an amine-containing diol, (vi) a catechol-containing species, (vii) an isocyanate, (viii) a polycarboxylic acid, and (x) one or more monomers comprising one or more alkyne moieties or one or more azide moieties. In other cases, a polymer or oligomer of a composition described herein comprises the reaction product of (i) a non-alkoxylated and non-alkenoxylated citric acid, citrate, or ester/amide of citric acid, e.g., a monomer of Formula (A1), and optionally an alkoxylated or alkenoxylated citric acid, citrate, or ester/amide of citric acid, e.g., a monomer of Formula (A2), with (ii) a polyol/polyamine such as a diol/diamine, and (iii) a monomer comprising an MRI contrast agent, (iv) an amino acid, (v) an amine-containing diol, (vi) a catechol-containing species, (vii) an isocyanate, (viii) a polycarboxylic acid, (ix) a diamine, and (x) one or more monomers comprising one or more alkyne moieties or one or more azide moieties.

Moreover, in some embodiments, the MRI-sensitive polymer or oligomer is formed from or is a reaction product of one or more monomers comprising one or more alkyne moieties and/or one or more azide moieties. For example, in some cases, a composition described herein comprises an MRI-sensitive polymer or oligomer formed from the following: one or more monomers of Formula (A1); optionally one or more monomers of Formula (A2); one or more monomers of Formula (B1) or (B2); optionally one or more monomers of Formula (F); optionally one of more monomers of Formula (K); optionally one or more monomers of Formula (C); optionally one or more monomers of Formula (D1), (D2), (D3), or (D4); optionally one or more monomers of Formula (E1) or (E2); optionally one or more monomers of Formula (G); one or more monomers comprising an MRI contrast agent; and one or more monomers comprising one or more alkyne moieties and/or one or more azide moieties. In some instances, the polymer is formed from monomers having a plurality of alkyne and/or azide moieties.

In addition, in some instances, a composition described herein comprises a plurality of MRI-sensitive polymers or oligomers as described herein, such as a first polymer formed from one or more one or more monomers of Formula (A1); optionally one or more monomers of Formula (A2); one or more monomers of Formula (B1) or (B2); one or more monomers of Formula (F); optionally one of more monomers of Formula (K); optionally one or more monomers of Formula (C); optionally one or more monomers of Formula (D1), (D2), (D3), or (D4); optionally one or more monomers of Formula (E1) or (E2); optionally one or more monomers of Formula (G); one or more monomers comprising an MRI contrast agent; and one or more monomers comprising one or more alkyne moieties; and a second polymer formed from one or more one or more monomers of Formula (A1); optionally one or more monomers of Formula (A2); one or more monomers of Formula (B1) or (B2); one or more monomers of Formula (F); optionally one of more monomers of Formula (K); optionally one or more monomers of Formula (C); optionally one or more monomers of Formula (D1), (D2), (D3), or (D4); optionally one or more monomers of Formula (E1) or (E2); optionally one or more monomers of Formula (G); and one or more monomers comprising one or more azide moieties. Further, in some cases, a composition described herein comprises an azide-alkyne cycloaddition product, such as a 1,4-triazole ring or 1,5-triazole ring. Such a cycloaddition product can be formed from one or more polymers described herein. For example, in some cases, a first polymer and a second polymer of a composition described herein can form a polymer network by forming one or more azide-alkyne cycloaddition products from monomers comprising one or more alkyne moieties and one or more monomers comprising one or more azide moieties.

Further, monomers comprising one or more alkyne and/or azide moieties used to form a polymer described herein can comprise any alkyne- and/or azide-containing chemical species not inconsistent with the objectives of the present disclosure. For example, in some instances, one or more such monomers comprise a polyol/polyamine such as a diol/diamine. Such a monomer, in some cases, can be incorporated into the polymer through the reaction of one or more hydroxyl moieties of the monomer with a carboxyl or carboxylic acid moiety of a monomer of Formula (A1) or of another carboxyl-containing monomer described herein, e.g., an optional monomer of Formula (A2). Moreover, in some instances, such a monomer can be used instead of the monomer of Formula (B1) or (B2). In other instances, such a monomer is used in conjunction with one or more monomers of Formula (B1) or (B2). Further, such a monomer can be a diazido-diol (DAzD) or an alkyne diol (AlD).

In some cases, one or more monomers comprising one or more azide moieties comprises a monomer of Formula (H1), (H2), or (H3):

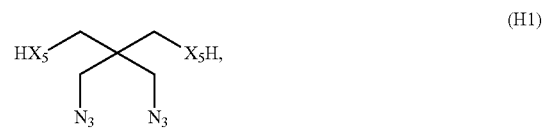

(H1)

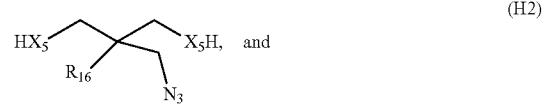

(H2)

(H3)

wherein $X_5$ is O or NH;
$R_{16}$ is —$CH_3$ or —$CH_2CH_3$; and
$R_{17}$ and $R_{18}$ are each independently —$CH_2N_3$, —$CH_3$, or —$CH_2CH_3$.

Further, the monomers of Formula (A1), optional (A2), (B1), (B2), (F), (H1), (H2), (H3), and the monomer comprising the MRI contrast agent can be used in any ratio not inconsistent with the objectives of the present disclosure. In addition, altering the ratios of monomers can, in some embodiments, alter the MRI activity, the antimicrobial properties, the biodegradability, the mechanical strength, and/or other properties of the polymer formed from the monomers. In some embodiments, the ratio of monomer (A1) or monomer (A2) to monomer (B1), monomer (B2), monomer (F), monomer (H1), monomer (H2), or monomer (H3) is between about 1:10 and about 10:1 or between about 1:5 and about 5:1. In some embodiments, the ratio is between about 1:4 and about 4:1. In some embodiments, the ratio is about 1:1. Further, in some embodiments, the ratio of the monomer comprising the MRI contrast agent to monomer (H1), monomer (H2), or monomer (H3) is between about 1:10 and about 10:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1.

Further, in some embodiments, one or more monomers comprising one or more alkyne moieties comprises a monomer of Formula (I1), (I2), (I3), (I4), (I5), or (I6):

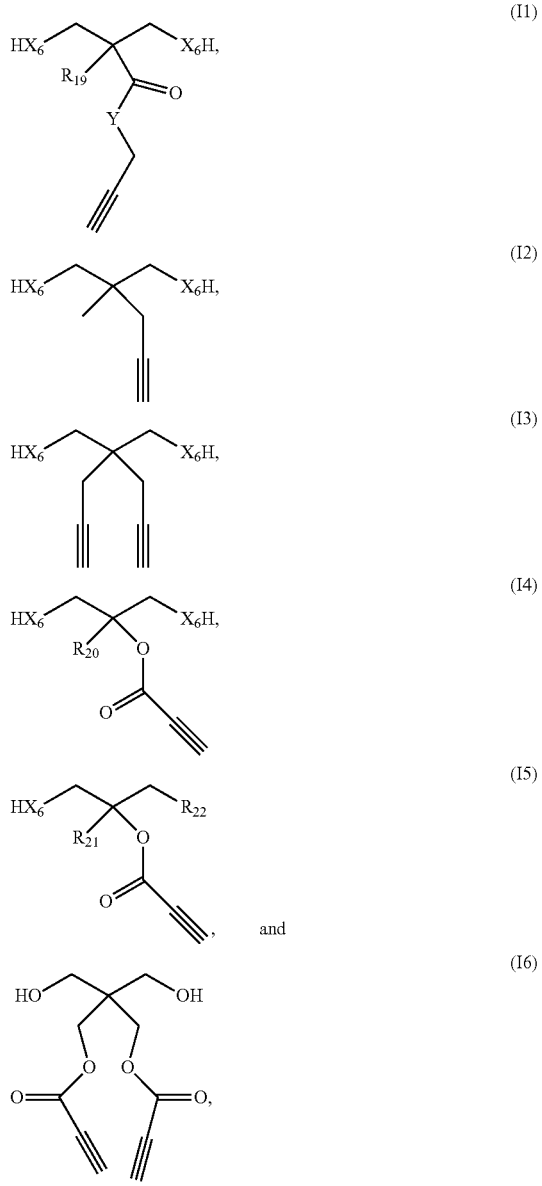

wherein $X_6$ and Y are each independently —O— or —NH—;
$R_{19}$ and $R_{20}$ are each independently —$CH_3$ or —$CH_2CH_3$;
$R_{21}$ is —O(CO)C≡CH, —$CH_3$, or —$CH_2CH_3$; and
$R_{22}$ is —$CH_3$, —OH or —$NH_2$.

Further, the monomers of Formula (A1), optional (A2), (B1), (B2), (F), (I1), (I2), (I3), (I4), (I5), (I6), and the monomer comprising the MRI contrast agent can be used in any ratio not inconsistent with the objectives of the present disclosure. In addition, altering the ratios of monomers can, in some embodiments, alter the MRI activity, the antimicrobial properties, the biodegradability, the mechanical strength, and/or other properties of the polymer formed from the monomers. In some embodiments, the ratio of monomer (A1) or monomer (A2) to monomer (B1), monomer (B2), monomer (F), monomer (I1), monomer (I2), monomer, monomer (I3), monomer (I4), monomer (I5), or monomer (I6) is between about 1:10 and about 10:1 or between about 1:5 and about 5:1. In some embodiments, the ratio is between about 1:4 and about 4:1. In some embodiments, the ratio is about 1:1. Further, in some embodiments, the ratio of the monomer comprising the MRI contrast agent to monomer (I1), monomer (I2), monomer (I3), monomer (I4), monomer (I5), or monomer (I6) is between about 1:10 and about 10:1. When (A2) is reacted, the ratio of monomer (A1) to monomer (A2), in some cases, is between about 1:10 and about 10:1 or between about 1:5 and about 5:1. In some embodiments, the ratio of monomer (A1) to monomer (A2) is between about 1:4 and about 4:1. In some embodiments, the ratio is about 1:1.

Additionally, in some embodiments, an MRI-sensitive polymer or oligomer described herein can be functionalized with a bioactive species. In some cases, the polymer is formed from an additional monomer comprising the bioactive species. Moreover, such an additional monomer can comprise one or more alkyne and/or azide moieties as described herein above. For example, in some instances, a polymer described herein is formed from one or more monomers comprising a peptide, polypeptide, nucleic acid, or polysaccharide, wherein the peptide, polypeptide, nucleic acid, or polysaccharide is functionalized with one or more alkyne and/or azide moieties. In some cases, the bioactive species is a growth factor or signaling molecule. Further, a peptide can comprise a dipeptide, tripeptide, tetrapeptide, or a longer peptide. As described further herein below, forming a polymer from such a monomer, in some embodiments, can provide additional biological functionality to a composition described herein.

In addition, in some embodiments, a composition described herein comprises a plurality of the polymers or oligomers described herein. In some instances, the polymers are selected to be reactive with one another through a click chemistry reaction scheme, as described above. In some cases, for example, a first polymer formed from one or more one or more monomers of Formula (A1); optionally one or more monomers of Formula (A2); one or more monomers of Formula (B1) or (B2); one or more monomers of Formula (F); optionally one of more monomers of Formula (K); optionally one or more monomers of Formula (C); optionally one or more monomers of Formula (D1), (D2), (D3), or (D4); optionally one or more monomers of Formula (E1) or (E2); optionally one or more monomers of Formula (G); one or more monomers comprising an MRI contrast agent; and one or more monomers comprising one or more alkyne moieties; and a second polymer formed from one or more one or more monomers of Formula (A1); optionally one or more monomers of Formula (A2); one or more monomers of Formula (B1) or (B2); one or more monomers of Formula (F); optionally one of more monomers of Formula (K); optionally one or more monomers of Formula (C); optionally one or more monomers of Formula (D1), (D2), (D3), or (D4); optionally one or more monomers of Formula (E1) or (E2); optionally one or more monomers of Formula (G); and one or more monomers comprising one or more azide moieties. Thus, in some such embodiments, a composition described herein can comprise an azide-alkyne cycloaddition product, such as a 1,4 or 1,5-triazole ring. In this manner, a first polymer and a second polymer of a composition described herein can form a polymer network by forming one or more azide-alkyne cycloaddition products to serve as cross-links of the polymer network. Other combinations of polymers are also possible.

A cross-linked polymer network described herein, such as a polymer network formed of click chemistry adducts, can have a high cross-linking density. "Cross-linking density," for reference purposes herein, can refer to the number of cross-links between polymer backbones or the molecular weight between cross-linking sites, calculated as described herein below. Further, in some embodiments, the cross-links of a polymer network described herein comprise azide-alkyne cycloaddition product cross-links. Cross-links may also include ester bonds formed by the esterification or reaction of one or more pendant carboxyl or carboxylic acid groups with one or more pendant hydroxyl groups of adjacent polymer backbones. In some embodiments, a polymer network described herein has a cross-linking density of at least about 500, at least about 1000, at least about 5000, at least about 7000, at least about 10,000, at least about 20,000, or at least about 30,000 mol/m$^3$. In some cases, the cross-linking density is between about 5000 and about 40,000 or between about 10,000 and about 40,000 mol/m$^3$.

It is also possible to form a polymer network using a click chemistry reaction scheme that does not necessarily form azide-alkyne cycloaddition products. For instance, in some cases, one or more monomers comprising an alkyne and/or azide moiety described herein can be at least partially replaced by one or more monomers comprising a different moiety that can participate in a click chemistry reaction scheme. For example, in some embodiments, a polymer or polymer network is formed from the reaction of one or more monomers comprising a thiol moiety with one or more monomers comprising an alkene (or alkyne) moiety through a thiol-ene/yne click reaction. Such a thiol-ene/yne click reaction can comprise the addition of an S—H bond across a carbon-carbon double bond or triple bond by a free radical or ionic mechanism. More generally, in some cases, a polymer described herein can be formed from one or more monomers comprising one or more first moieties operable to participate in a click chemistry reaction and/or one or more second moieties operable to participate in the same click chemistry reaction, where the first and second moieties differ. Any click chemistry reaction not inconsistent with the objectives of the present disclosure may be used. In some instances, the click chemistry reaction comprises a [3+2] cycloaddition such as a Huisgen alkyne-azide cycloaddition; a thiol-ene/yne reaction; a Diels-Alder reaction; an inverse electron demand Diels-Alder reaction; a [4+1] cycloaddition such as the cycloaddition reaction of an isocyanide with a tetrazine; or a nucleophilic substitution reaction involving a strained ring such as an epoxy or aziridine ring. Not intending to be bound by theory, it is believed that the use of a click chemistry reaction scheme to provide cross-linking in a polymer network can, in some cases, improve the mechanical strength of a polymer network without sacrificing pendant citric acid carboxyl moieties for other purposes, such as hydroxyapatite (HA) calcium chelation.

Moreover, in some instances, the polyol/polyamine above can be at least partially replaced by an alcohol having only one hydroxyl group or by an amine or an amide. Further, in some cases, the polyol/polyamine can be at least partially replaced by a polymer or oligomer having one or more hydroxyl, amine, or amide groups. Such a polymer or oligomer, in some instances, can be a polyester, polyether, or polyamide. Thus, in some embodiments, a composition described herein comprises the reaction product of (i) a non-alkoxylated and non-alkenoxylated citric acid, citrate, or ester/amide of citric acid with (ii) an alcohol, amine, amide, polyester, polyether, or polyamide and (iii) a monomer comprising and MRI contrast agent, and (x) a monomer comprising an alkyne moiety and/or an azide moiety. In some embodiments, a composition described herein comprises the reaction product of (i) a non-alkoxylated and non-alkenoxylated citric acid, citrate, or ester/amide of citric acid with (ii) an alcohol, amine, amide, polyester, polyether, or polyamide and (iii) a monomer comprising and MRI contrast agent, (iv) an amino acid monomer, and (x) a monomer comprising an alkyne moiety and/or an azide moiety.

The monomers of Formula (A1), optional (A2), (B1), (B2), (F), the monomer comprising the MRI contrast agent, and the monomers comprising one or more alkyne and/or azide moieties can be used in any ratio not inconsistent with the objectives of the present disclosure. In addition, altering the ratios of monomers can, in some embodiments, alter the biodegradability, the MRI activity, the mechanical strength, and/or other properties of the polymer formed from the monomers. In some embodiments, the ratio of monomer (A1) or monomer (A2), if reacted, to monomer (B1), (B2), or (B3) is between about 1:10 and about 10:1 or between about 1:5 and about 5:1. In some embodiments, the ratio of monomer (A1) or monomer (A2), if reacted, to monomer (B1), (B2), or (B3) is between about 1:4 and about 4:1. In some embodiments, the ratio is about 1:1. The ratio of an alkyne or azide-containing monomer to a monomer of Formula (A1), optional (A2), (B1), or (B2) can be between about 1:20 and 1:2 or between about 1:10 and about 1:3.

A polymer network described herein can be prepared in any manner not inconsistent with the objectives of the present disclosure. In some cases, a method of making a polymer network comprises mixing and/or reacting a first polymer and a second polymer, the first and second polymer each comprising a polymer of a composition described herein. Moreover, the first and second polymers can comprise complementary functional groups for carrying out a cross-linking reaction, including through a click chemistry reaction scheme. For example, in some instances, the first polymer comprises one or more alkyne moieties, and the second polymer comprises one or more azide moieties. In some cases, the first polymer is formed from one or more monomers of Formula (A1); optionally one or more monomers of Formula (A2); one or more monomers of Formula (B1) or (B2); one or more monomers of Formula (F); one or more monomers comprising a MRI contrast agent, and one or more monomers comprising one or more alkyne moieties; and the second polymer is formed from one or more monomers of Formula (A1); optionally one or more monomers of Formula (A2); one or more monomers of (B1) or (B2); and one or more monomers comprising one or more azide moieties. In such cases, the polymer network may be formed by reacting the one or more alkyne moieties of the first polymer with the one or more azide moieties of the second polymer to form one or more azide-alkyne cycloaddition products.

Reacting the alkyne and azide moieties can be carried out in any manner not inconsistent with the objectives of the present disclosure. In some embodiments, reacting the alkyne and azide moieties comprises heating the mixture of the first and second polymers to a temperature sufficient to induce a cross-linking reaction, such as a temperature of about 80° C. to about 120° C. to induce a thermal click chemistry reaction or an esterification reaction. Alkyne and azide moieties may also be reacted by providing a catalyst to the mixture, such as a metal catalyst. A metal catalyst suitable for use in some embodiments described herein can include one or more of copper, ruthenium, and silver. In other instances, a metal-containing catalyst such as a copper catalyst is not used. Further, reacting the alkyne and azide moieties of first and second polymers described herein can comprise inducing a click chemistry reaction between the azide and alkyne moieties. Such a click chemistry reaction can be a thermal click chemistry reaction or another type of click chemistry reaction, such as a strain promoted alkyne-azide cycloaddition (SPAAC) or a copper-catalyzed alkyne-azide cycloaddition (CuAAC). Moreover, carrying out a reaction between alkyne and azide moieties in a manner described herein can form a cross-linked polymer network, the cross-links of the network being formed by azide-alkyne cycloaddition reaction products such as 1,4- or 1,5-triazole rings. Additionally, in some embodiments, the first and/or second polymers can comprise one or more additional moieties that can form additional cross-links to provide a polymer network. For example, in some cases, the first polymer and/or the second polymer comprises one or more carboxylic acid groups and/or hydroxyl groups. In some such instances, additional cross-linking can occur through the formation of one or more ester bonds between the carboxylic acid and hydroxyl groups.

Moreover, in some embodiments, a method of making a polymer network described herein further comprises functionalizing the surface of the polymer network with one or more biofunctional species, such as one or more peptides, polypeptides, nucleic acids, and/or polysaccharides. Such functionalization can be carried out in any manner not inconsistent with the objectives of the present disclosure. For example, in some instances, a method described herein further comprises reacting one or more of a peptide, polypeptide, nucleic acid, and polysaccharide with a pendant alkyne and/or azide moiety on the cross-linked polymer network to provide a covalent bond between the cross-linked polymer network and the peptide, polypeptide, nucleic acid, and/or polysaccharide. In some cases, the peptide, polypeptide, nucleic acid, and/or polysaccharide comprises an alkyne or azide moiety, and formation of a covalent bond is carried out by inducing a further click chemistry reaction, such as a strain-promoted alkyne-azide cycloaddition reaction, between one or more alkyne and/or azide moieties of the polymer network and one or more alkyne and/or azide moieties of the peptide, polypeptide, nucleic acid, and/or polysaccharide. Such a reaction, in some instances, can be carried out at 37° C. in an aqueous environment. Additionally, a peptide, polypeptide, or other biofunctional species can be modified to be clickable by reacting the peptide, polypeptide, or other species with a reagent such as a Click-easy® BCN N-hydroxysuccinimide ester, commercially available from Berry & Associates.

As described hereinabove, compositions described herein can provide antibacterial and/or antifungal activity through the inclusion of one or more monomers of Formula (A2) even without the use or inclusion of separately provided antibiotic and/or antifungal agents other than the polymer or oligomer of the compositions. However, if desired, it is also possible to include such additional antibiotic and/or antifungal agents in a composition described herein. For example, in some cases, a composition described herein further comprises a drug dispersed in the polymer or oligomer. Such drugs may include, but are not limited to, antibiotics, antifungals, antimicrobial peptides, and/or antimicrobial inorganic compositions such as metal particles. Antibiotics can include bactericidal materials such as penicillins, cephalosporins, polymyxins, rifamycins, lipiarmycins, quinolones, and sulfonamides. Antibiotics can also include bacteriostatic materials such as macrolides, lincosamides and tetracyclines or cyclic lipopeptides, glycylcyclines, oxazolidinones, and lipiarmycins. Antifungals can include fungicidal materials such as amphotericin B, azole antifungals, echinocandins, or flucytosine.

Moreover, in some embodiments, a composition described herein comprising a polymer network can further comprise a particulate material dispersed in the polymer network. Polymer networks are described herein and are understood to refer to a structure in which polymer chains are interconnected. For example, a polymer network may be formed by cross-linking discrete polymer chains, i.e., intermolecular cross-linking, or by intramolecular cross-linking. In a polymer network 10% or more, 20% or more, 30% or more, 40% or more, 50% or more, 60% or more, 70% or more, 80% or more, 90% or more or about 100% of the polymers may be cross-linked through covalent bonds or otherwise interconnected through non-covalent bonds such as ionic bonds. Any particulate material not inconsistent with the objectives of the present disclosure may be used. In some cases, the particulate material comprises one or more of hydroxyapatite, tricalcium phosphate, biphasic calcium phosphate, bioglass, ceramic, magnesium powder, magnesium oxide, magnesium alloy, and decellularized bone tissue particles. Other particulate materials may also be used, such as silver nanoparticles.

In addition, a particulate material described herein can have any particle size and/or particle shape not inconsistent with the objectives of the present disclosure. In some embodiments, for instance, a particulate material has an average particle size in at least one dimension of less than about 1000 µm, less than about 800 µm, less than about 500 µm, less than about 300 µm, less than about 100 µm, less than about 50 µm, less than about 30 µm, or less than about 10 µm. In some cases, a particulate material has an average particle size in at least one dimension of less than about 1 µm, less than about 500 nm, less than about 300 nm, less than about 100 nm, less than about 50 nm, or less than about 30 nm. In some instances, a particulate material has an average particle size recited herein in two dimensions or three dimensions. Moreover, a particulate material can be formed of substantially spherical particles, plate-like particles, needle-like particles, or a combination thereof. Particulate materials having other shapes may also be used.

A particulate material can be present in a composition described herein in any amount not inconsistent with the objectives of the present disclosure. For example, in some cases, a composition comprises up to about 70 weight percent, up to about 60 weight percent, up to about 50 weight percent, up to about 40 weight percent, or up to about 30 weight percent particulate material, based on the total weight of the composition. In some instances, a composition comprises between about 1 and about 70 weight percent, between about 10 and about 70 weight percent, between about 15 and about 60 weight percent, between about 25 and about 65 weight percent, between about 25 and about 50 weight percent, between about 30 and about 70 weight percent, between about 30 and about 50 weight percent, between about 40 and about 70 weight percent, or between about 50 and about 70 weight percent, based on the total weight of the composition. For example, in some cases, a composition comprising a polymer network described herein comprises up to about 65 weight percent hydroxyapatite.

Moreover, in some embodiments, a composition described herein can comprise a high amount of particulate material, such as an amount up to about 70 weight percent, even when the polymers used to form the polymer network have a low weight average molecular weight, such as a weight average molecular weight of less than about 2000, less than about 1000, or less than about 500. For example, in some instances, a composition described herein comprises a polymer network formed from a polymer described herein having a weight average molecular weight of less than about 2000, less than about 1000, or less than about 500, and further comprises hydroxyapatite particles dispersed in the polymer network in an amount up to about 70 weight percent. Additionally, in some cases, the polymer network is not cross-linked or substantially cross-linked, other than by any cross-linking that may be provided by the hydroxyapatite particles.

Further, a particulate material described herein can be dispersed in a polymer network in any manner not inconsistent with the objectives of the present disclosure. In some embodiments, for instance, the particulate material is mixed or ground into the polymer network. In addition, a particulate material described herein, in some cases, can be chelated or otherwise bound by one or more pendant functional groups of the polymer network. For instance, in some cases, a composition comprises hydroxyapatite particles dispersed in a polymer network described herein, wherein the hydroxyapatite is chelated by one or more pendant functional groups of the polymer network. In some embodiments, one or more carboxyl moieties or one or more citrate moieties of the polymer network chelate one or more calcium-containing portions of the hydroxyapatite.

II. MRI-Active or -Sensitive and Luminescent Compositions

In one aspect, MRI-sensitive and luminescent compositions are described herein. Such a "luminescent composition" can be phosphorescent or fluorescent. A luminescent composition described herein may, more particularly, be photoluminescent. In some embodiments, a luminescent composition may comprise one or more luminescent polymers or oligomers. These polymers or oligomers may include polymers or oligomers that are both photoluminescent and MRI-sensitive, i.e., polymers or oligomers that have a photoluminescent and MRI contrast agent moiety, and polymers or oligomers that are photoluminescent, but not MRI-sensitive, i.e., polymers or oligomers that have a photoluminescent moiety, but not an MRI contrast agent moiety. For example, the polymers or oligomers may include photoluminescent citrate-containing MRI active polymers or oligomers as described hereinabove or citrate-containing polymers as described hereinabove, that are photoluminescent, but not MRI-sensitive, i.e., are not formed from a monomer comprising an MRI contrast agent. The compositions herein may also comprise a separately added phosphor or fluorophore. However, when photoluminescent polymers or oligomers are added, the use of separately provided phosphors or fluorophores is not necessary for the compositions to be luminescent.

The photoluminescent citrate-containing polymers or oligomers described herein comprise, consist of, or consist essentially of a photoluminescent moiety in the backbone of or pendant to the backbone of the citrate-containing polymers or oligomers described herein. In some embodiments, the photoluminescent moiety is formed upon reaction of the monomers described herein above to form the citrate-containing polymers or oligomers. For example, in FIG. 1, the photoluminescent moiety is a dioxo-pyridine ring, which is formed upon reaction of citric acid, i.e., a non-alkoxylated and non-alkenoxylated citric acid, with 1,8-octainediol, i.e., a polyol, L-serin, i.e., an amino acid, MDEA, i.e., a amine-containing diol, and Gd-DTPA, i.e., a monomer comprising an MRI contrast agent. None of the reactants had a dioxo-pyridine ring. In some other embodiments, the photoluminescent moiety might be a thiazolopyridine acid (TPA). In some embodiments, the photoluminescent moiety may be a part of one of the monomers that are reacted to form the citrate-containing polymers described herein.

A photoluminescent polymer or oligomer described herein, in some instances, can exhibit a fluorescence emission profile centered in the visible or near infrared (NIR) region of the electromagnetic spectrum. For example, in some embodiments, a luminescent or fluorescent polymer or oligomer described herein, in some instances, exhibits a luminescence or fluorescence emission profile centered at a wavelength between about 350 nm and about 750 nm, between about 390 nm and about 725 nm, between about 430 nm and about 650 nm, or between about 500 nm and about 700 nm. Moreover, in some implementations, a luminescent or fluorescent polymer or oligomer described herein resists photobleaching and/or has superior photobleaching characteristics compared to some other organic dyes.

It has been found that citrate-containing polymers or oligomers as described herein that are both MRI-sensitive and photoluminescent exhibit stronger photoluminescence, particularly fluorescence, in the NIR region, compared to the same citrate-containing polymers or oligomers that are photoluminescent, but are not MRI-sensitive. What is meant by "the same citrate-containing polymers or oligomers that are photoluminescent, but are not MRI-sensitive" is that the polymers are oligomers are formed from the same monomers, except that a monomer comprising a MRI contrast agent is not reacted to form the citrate-containing polymers or oligomers that are photoluminescent, but are not MRI-sensitive. Without wishing to be bound by any particular theory, it is believed that this observed increase in fluorescence in the NIR region may be due to a decrease in self-quenching of the NIR wavelengths emitted by the photoluminescent moiety of the polymers or oligomers by an absorbing moiety of the polymers or oligomers. It is believed that an increase in the distance between the photoluminescent moiety and the absorbing moiety may be responsible for this increase in fluorescence in the NIR region.

III. Methods of Imaging

In one aspect, a method of imaging a biological environment or compartment is disclosed herein. The method is not so limited and may comprise, consist of, or consist essentially of a step of disposing the MRI-sensitive and/or MRI-sensitive and photoluminescent compositions described herein above into a biological environment. Such an environment, in some instances, comprises or consists essentially of a cell, tissue, organ, or body cavity of a living animal or mammal, such as a human. A biological environment may comprise a subcutaneous area, including a subcutaneous area that is under or deep under layers of muscle tissues.

The disposition of the compositions into the biological environment is not so limited. For example, the compositions may be injected or implanted into a biological environment. In some preferred embodiments, the compositions described herein may be disposed into a biological environment as part of a graft or scaffold, which can be implanted subcutaneously, including in a subcutaneous area that is under or deep under layers of muscle tissues.

A "graft" or "scaffold," for reference purposes herein, can refer to any structure usable as a platform or implant for the replacement of missing bone or for promotion of growth of new bone. Moreover, as utilized herein, the terms "graft" or "scaffold" may be synonymous. For example, a graft or scaffold utilized in a method described herein can be used in the repair of a bone defect, the replacement of missing or removed bone, or for the promotion of new bone growth, as in the case of a bone fusion procedure. Further, it is to be understood that grafts or scaffolds consistent with methods described herein can have any structure or be formed in any shape, configuration, or orientation not inconsistent with the objectives of the present invention. For example, in some embodiments, a graft or scaffold can be shaped, configured, or oriented in such a manner as to correspond to a defect or bone growth site to be repaired. For example, a graft or scaffold utilized in the repair of a bone defect, such as a calvarial defect, may be formed, molded, or resized to a size and/or shape corresponding to the defect. In certain other cases, such as in a bone fusion procedure, a graft or scaffold utilized in methods described herein can have a shape, configuration, orientation, or dimensions adapted to traverse a gap between the bones to be fused and/or to reinforce a bone growth site. In this manner, particular shapes, sizes, orientations and/or configurations of grafts or scaffolds described herein are not intended to be limited to a particular set or subset of modalities on, within, or adjacent to a bone growth site. A "bone growth site," as referenced herein, can be any area in which bone growth or repair may be desired. In certain non-limiting examples, a bone growth site can comprise or include a bone defect, a site in which bone has been removed or degraded, and/or a site of desired new bone growth, as in the case of a spinal or other bone fusion.

The graft or scaffold of a method described herein, in some cases, can comprise a particulate inorganic material dispersed within a polymer network. The polymer network of a graft or scaffold described herein can comprise or be formed from any of the compositions described herein, which have been cross-linked to form a polymer network.

In other embodiments, the method of imaging a biological environment may comprise, consist of, or consist essentially of the disposing step and magnetic resonance imaging (MRI) steps. The MRI steps may comprise, consist of, or consist essentially of the following steps: (1) exposing the biological environment to radio-frequency electromagnetic radiation while the biological environment is disposed in a magnetic field, thereby exciting hydrogen atoms of the biological environment, and then, (2) detecting relaxation of the excited hydrogen atoms.

In other embodiments, the method of imaging a biological environment may comprise, consist of, or consist essentially of the disposing step and photoluminescence imaging steps. The photoluminescence imaging steps may comprise, consist of, or consist essentially of the following steps: (1) exposing the biological environment to electromagnetic radiation having a wavelength corresponding to an excitation wavelength of a luminescent moiety of the disposed polymer or oligomer, and then (2) detecting light emitted by the luminescent moiety. In these embodiments, the disposed compositions are MRI-sensitive and photoluminescent compositions as described herein. In some preferred embodiments, the luminescent moiety may comprise a dioxopyridine ring (DPR) or a thiazolopyridine acid (TPA).

In other embodiments the method of imaging a biological environment may be a dual-imaging method. For example, the dual imaging may comprise, consist of, or consist essentially of, in addition to the disposing step, a magnetic resonance imaging step and a photoluminescence imaging step, e.g., a fluorescence imaging step. The dual-imaging method may comprise, consist of, or consist essentially of the disposing step and the following additional steps: (1) exposing the biological environment to electromagnetic radiation having a wavelength corresponding to an excitation wavelength of a luminescent moiety of the disposed polymer or oligomer, and then detecting light emitted by the luminescent moiety; and (2) exposing the biological environment to radio-frequency electromagnetic radiation while the biological environment is disposed in a magnetic field, thereby exciting hydrogen atoms of the biological environment, and then, detecting relaxation of the excited hydrogen atoms. These additional steps may be performed in any order. For the dual-imaging methods, the MRI-sensitive and photoluminescent compositions described herein are preferably used.

In some additional embodiments, the method of imaging a biological environment may be a 3D imaging method, where the dimensions are photoluminescence, e.g., fluorescence, MRI, and size/geometry. In further embodiments, the method of imaging a biological environment may be a 4D imaging method wherein the fourth dimension is time and degradation of time. This fourth dimension is possible due to the degradability, particularly the biodegradability, of some of the compositions disclosed herein.

IV. Films, Grafts, or Scaffolds

In another aspect films, grafts, or scaffolds are described herein. The films, grafts, or scaffolds may comprise, consist of, or consist essentially of the MRI-sensitive or MRI-sensitive and photoluminescent compositions described herein.

The graft or scaffold of a method described herein, in some cases, can comprise a particulate inorganic material dispersed within a polymer network. The polymer network of a graft or scaffold described herein can comprise or be formed from any of the compositions described herein, which have been cross-linked to form a polymer network.

EXAMPLES

Some embodiments described herein are further illustrated in the following non-limiting examples.

1. Synthesis of BPLPMGd Prepolymers

All chemicals were purchased from Sigmae-Aldrich, and were used as received without further purification, except where mentioned otherwise.

Prepolymers with different molar ratios of Gd-DTPA were synthesized by reacting citric acid (CA), 1,8-octanediol (OD), L-serine, N-methyldiethanolamine, and Gd-DTPA through the thermal polycondensation reaction as shown in FIG. 1. Prepolymers formed from these monomers were called BPLPMGd prepolymers. The theoretical mole ratios of Gd-DTPA to CA in these BPLPMGd prepolymers were set as 0, 0.02, 0.04 and 0.06, respectively. Obtained polymers were named as BPLPMGd0, BPLPMGd0.02, BPLPMGd0.04, BPLPMGd0.06, respectively.

2. Preparation of BPLPMGd Films, Scaffolds, and Nanoparticles

BPLPMGd films were prepared by casting their dioxane solution into Teflon molds and followed by evaporation and heat crosslinking at 80° C. for 2 days. BPLPMGd porous scaffolds were fabricated via a conventional particulate-leaching method with controlled pore sizes, porosity, and interconnectivity.

3. Characterization

BPLPMGd pre-polymers were dissolved in 1,4-dioxane to acquire photoluminescence spectra with a ORIBA Scientific Fluoromax-4 spectrofluorometer. Both the excitation and the emission slit widths were set at 1.5 nm. Fluorescence imaging of BPLPMGd scaffolds was conducted on a Maestro fluorescence imaging system. For MR measurement, the BPLPMGd scaffolds were embedded in 1.5% (w/v) agarose gel, and MR related signals and data of labeled scaffolds were performed in a 7 T Bruker system (Bruker, Billerica, MA) at room temperature.

In Vitro Cell Culturing Studies on BPLPAT Films and Scaffolds

Degradation cytotoxicity: The relative cytotoxicity of degradation products were quantitatively assessed by Cell Counting Kit-8 (CCK-8) assay against 3T3 fibroblasts. Poly(lactide-co-glycolide) (PLGA5050) film was used as a control. Polymer films (1g) were fully degraded in 10 mL of 2 M NaOH solution. The pH adjusted (pH 7.4) degradation products to were then diluted by 1×, 10× and 100× times with PBS. All the solutions were sterilized before filtered cell culturing. 3T3 fibroblasts with a seeding density of 5×10$^4$ cell/mL suspended in 200 µL culture medium was added into each well of a 96 well plate. The cells were then incubated at 37° C., 5% $CO_2$ and 95% humidity for 24 hours. 20 µL of diluted degradation solution was added to each well. After another 24 hours culturing, CCK-8 was applied to test cell viability.

Cytotoxicity and Cell Proliferation Studies on BPLPMGd Films: To test the cytotoxicity of polymer films, films were cut in round shape to fit 96 well plates. The films were sterilized by treating with 70% ethanol, UV light, and culture media in sequence. 200 µL of the cell suspension in culturing media with the density of 5×10$^4$ cells/mL was added to each well in a 96-well plate with a film sample on the bottom. CCK-8 was applied to test cell viability after 24 hours. For cell proliferation study, 200 L cell suspension with the density of 1×10$^4$ cells/mL was applied. Cell viability at time points of 1, 3, 5, and 7 days were recorded.

Cell Growth on BPLPMGd Scaffolds: To study the cell growth on BPLPMGd scaffolds, 3T3 fibroblasts were seeded at a density of 1×10$^6$ cells/mL in cell culture media on BPLPMGd scaffolds. After cell culturing for 7 days, the scaffolds fixed with 2.5% glutaraldehyde were used for SEM study.

In Vivo Fluorescence Imaging

The intensity of the fluorescence emitted from the scaffold decreased significantly over time while using the same exposure time and aperture, so the image threshold (0.01-0.15) was adjusted to localize the scaffold and extract the profile of its fluorescence area. The total image intensity within this profile was calculated (the value of each pixel varies from 0 to 1). Although the area size of this profile may vary by the segmenting threshold, the total intensity shows ignorable small variations.

In Vivo MRI Experiment

Rats were anesthetized using 4% isoflurane, then placed in supine position and secured on a self-made half-cylinder holder using ear bars. Isoflurane at 2.0% was continuously delivered via a nose cone to the rat during the whole experiment. A thermometer was placed in the rat's anal to monitor its body temperature. The rat was further placed into a Varian volume coil, which is used to emit radio frequency pulses and receive MRI signals. During the MRI experiment, heated air was plumping into the bold of the scanner to maintain the rat's body temperature at 37° C. The rat was scanned in a 7T Varian Scanner using a Bruker Console. The T1_Map_RARE sequence was used to acquire T1-weighted images (Field of view=50'50 mm, matrix size=256'192, slice thickness=0.8 mm, 12-24 slices, repetition time=6000, 4500, 3000, 2000, 1000 and 550 s, echo time=8 ms, 6 T1 experiment times).

MRI Data Processing

For the MRI data, the T1-weighted images were in 4D format: 3D for the spatial information and 1D for the variable repetition time (TR). For each 3D voxel, its T1-weighted signal intensity was acquired at six different TRs (6000, 4500, 3000, 2000, 1000 and 550 s). The profile of the implanted scaffold was manually drawn slice by slice based on the image acquired at TR=6000 s. The volume of this scaffold was calculated by multiplying the voxel number inside the profile and the voxel size. Then the T1-weighted image intensity of the scaffold was regionally averaged at each TR. This T1 data was fitted to the standard inversion recovery curve $M(t)=M_0(1-2a'exp(t/T1))$, providing the equilibrium tissue magnetization $M_0$, which was regarded as the proton density for further analysis (Mathematica 11.0, Wolfram Research Inc., Champaign, IL, USA).

4. Results and Discussion

In Vitro Photoluminescence Properties of BPLPMGd Solutions and Scaffolds

Figure 2A:
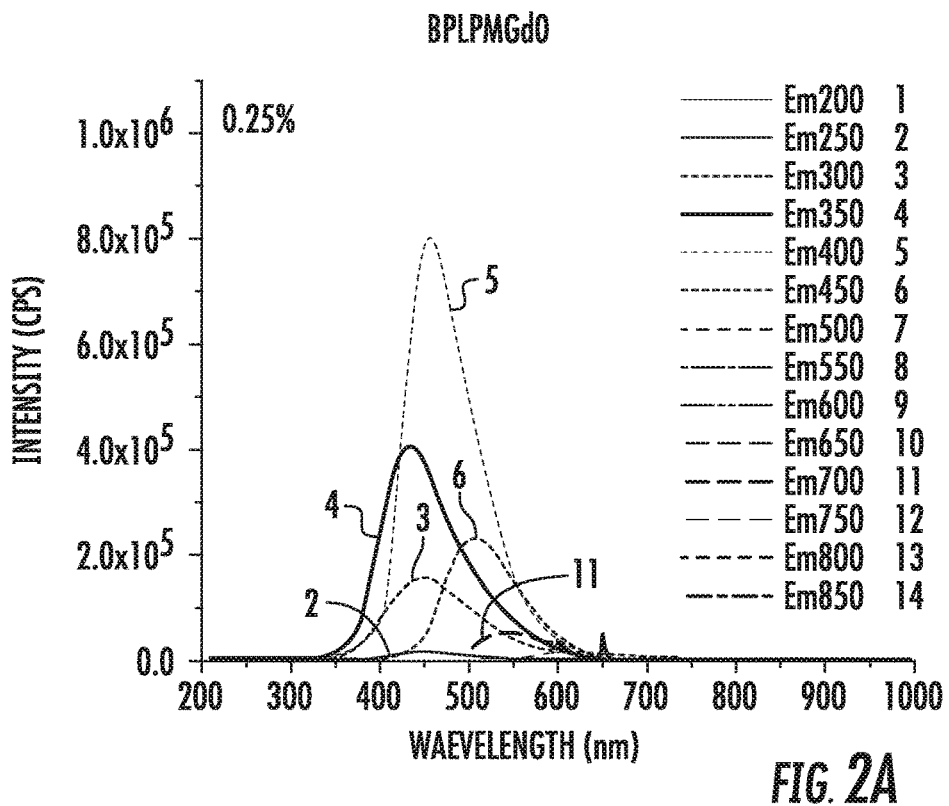
FIG. 2(a) is a fluorescence spectrum of a BPLPMGd 0 solution.
Figure 2B:
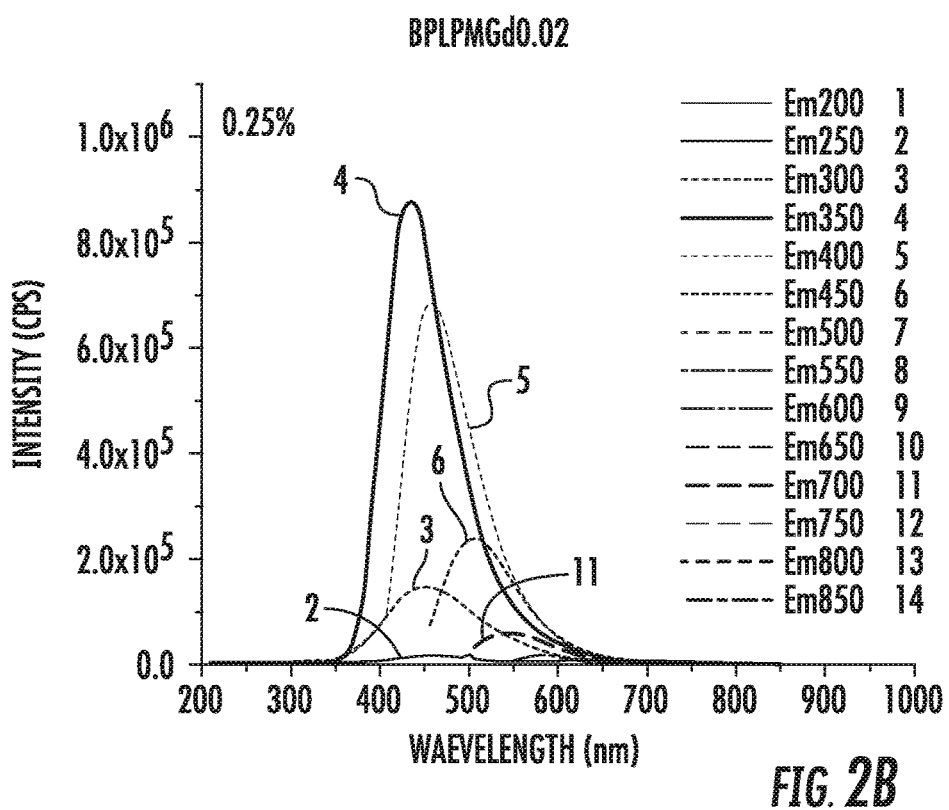
FIG. 2(b) is a fluorescence spectrum of a BPLPMGd 0.02 solution.
Figure 2C:
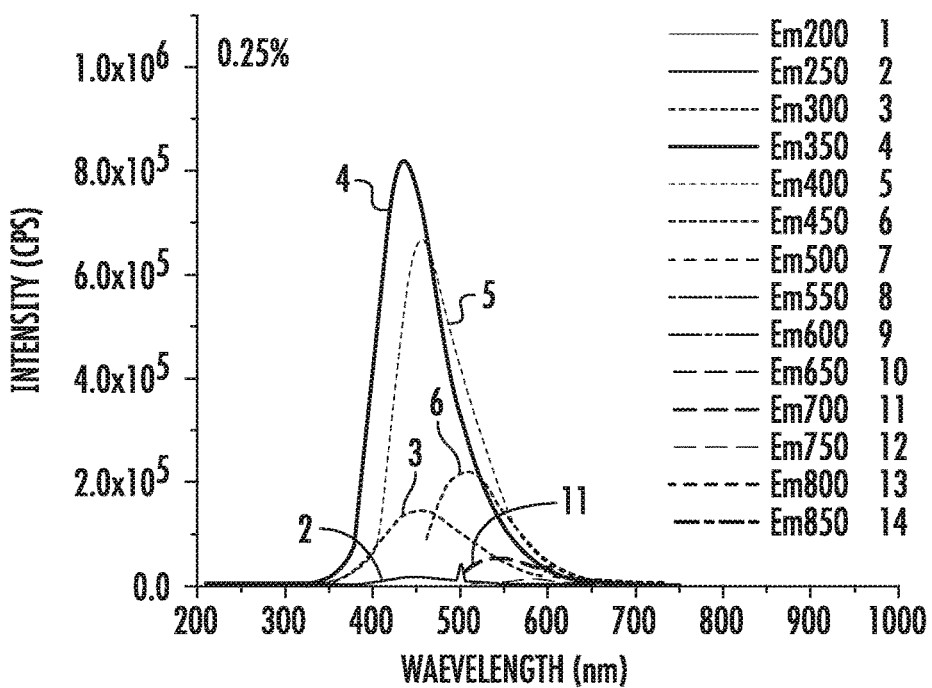
FIG. 2(c) is a fluorescence spectrum of a BPLPMGd 0.04 solution.
Figure 2D:
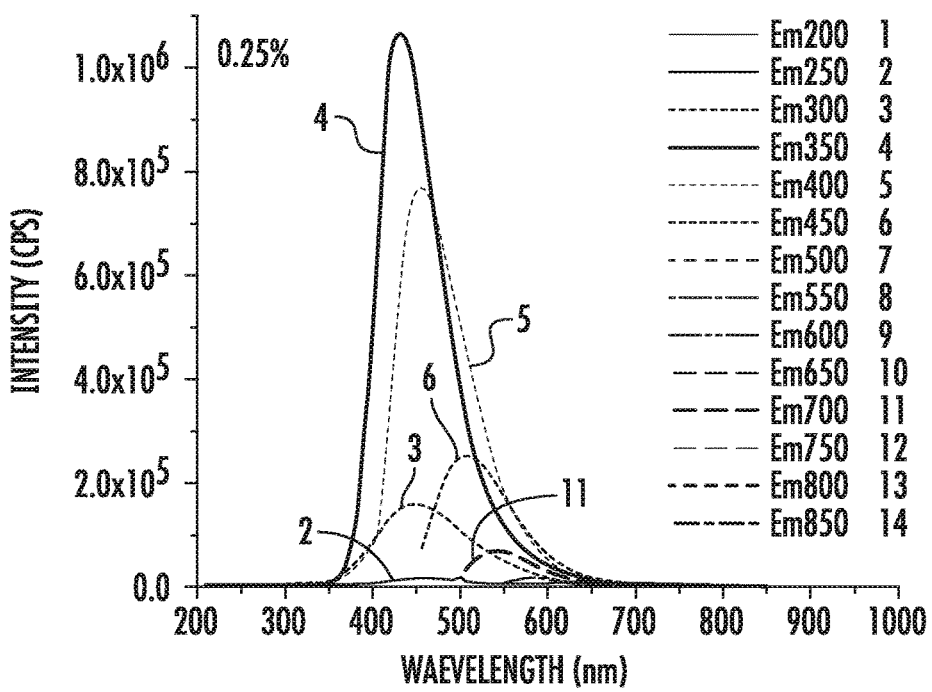
FIG. 2(d) is a fluorescence spectrum of a BPLPMGd0.06 solution.
Figure 3:
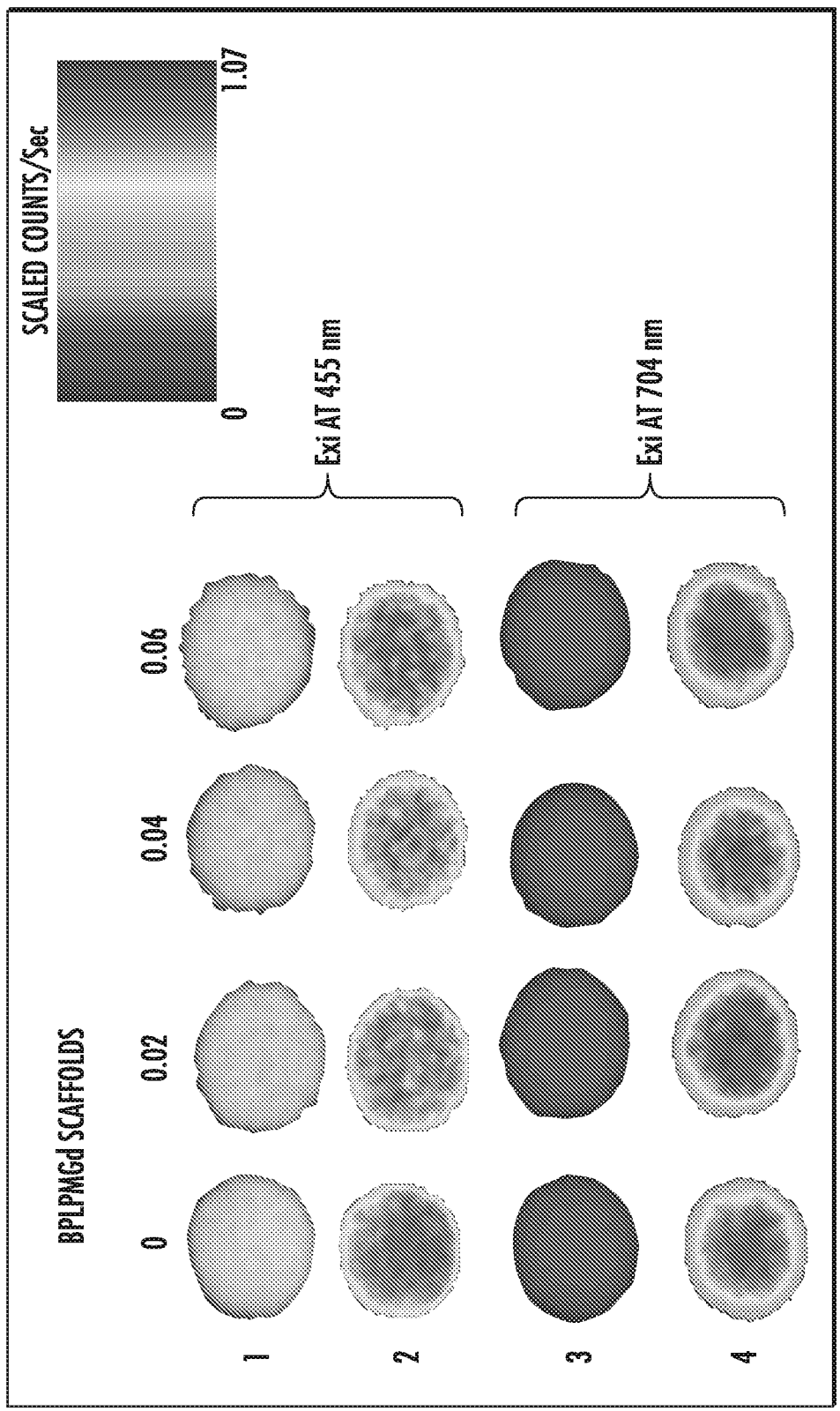
FIG. 3 includes fluorescent images (rows 1 and 3) and fluorescent intensity maps (rows 2 and 4) of BPLPMGd scaffolds with different ratios of Gd-DTPA for various excitation wavelengths.

In photoluminescence properties study of BPLPMGd solutions, different BPLPMGd (BPLPMGd0, BPLPMGd0.02, BPLPMGd0.04 and BPLPMGd0.06) solutions at the concentration of 0.25% (m/V) were tested with the spectrofluorometer. As presented in FIGS. 2(a), (b), (c), and (d), all BPLPMGd solutions present red shift emission spectra with the increasing of excitation wavelengths (from 200 nm to 850 nm). Fluorescence imaging capability of BPLPMGd scaffolds was proved by the Maestro fluorescence imaging system. After being excited by lights at a broad range of wavelengths (455 nm, 523 nm, 595 nm, 605 nm, 635 nm, 661 nm, 704 nm, and 735 nm), BPLPMGd scaffolds with different ratios of Gd-DTPA exhibit bright fluorescent images (FIG. 3, rows 1 and 3) and strong fluorescent intensity maps (FIG. 3, rows 2 and 4).

In Vitro Magnetic Resonance Studies of BPLPMGd Scaffolds

Figure 4A:
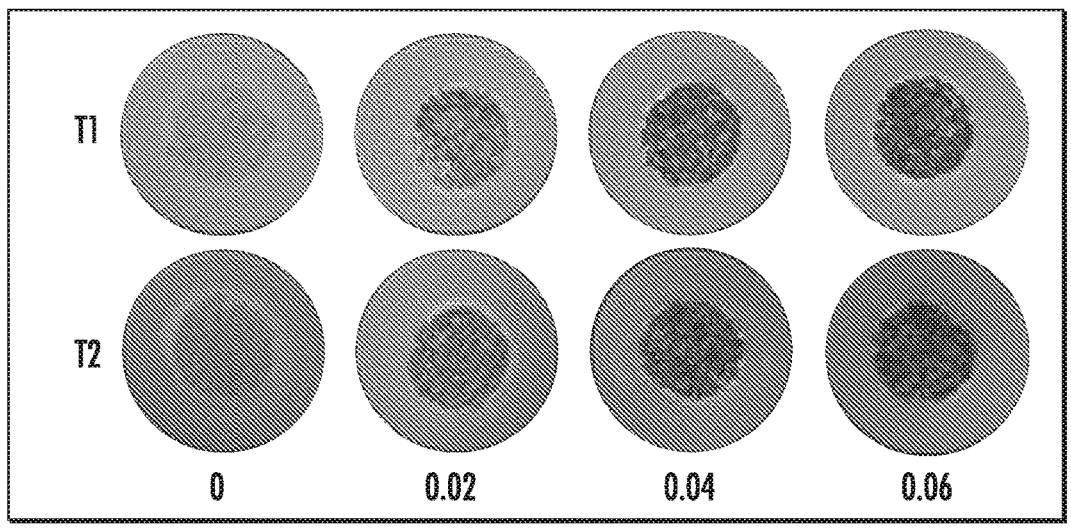
FIG. 4(a) is T1 and T2 images of BPLPMGd scaffolds with different ratios of DTPA.
Figure 4B:
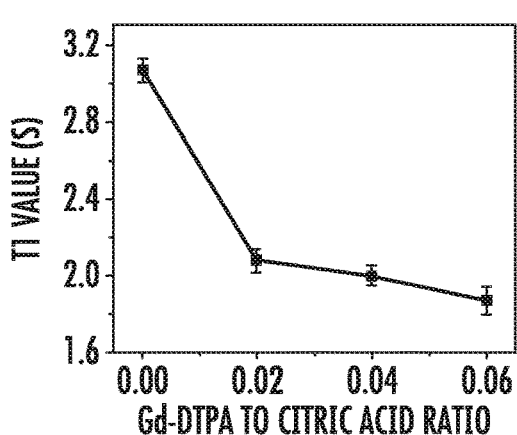
FIG. 4(b) is a graph of the T1 values.
Figure 4C:
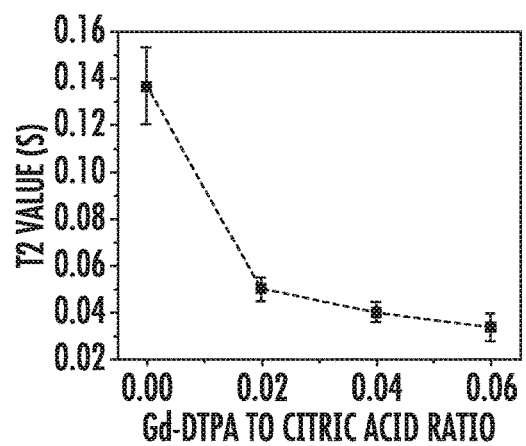
FIG. 4(c) is a graph of the T2 values.
Figure 4D:
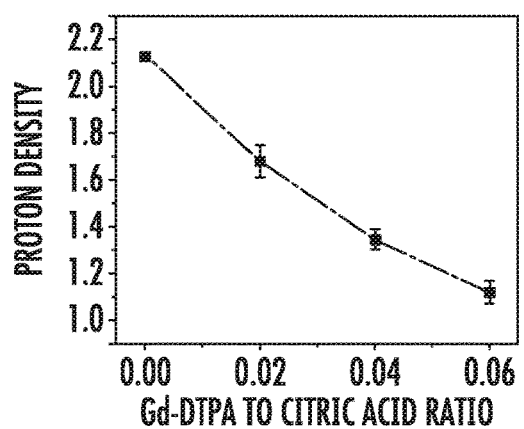
FIG. 4(d) is a graph of the proton density values of BPLPMgd scaffolds with different ratios of Gd-DTPA.

The scaffolds were visualized with T1- and T2-weighted MRI, and the corresponding T1, T2 and proton density values were calculated based on relaxometry measurements. Preliminary data indicated that both T1- and T2-weighted images of BPLPMGd scaffolds showed decreased intensity with the increase of Gd-DTPA ratios (FIG. 4(a)). Significant decreases in T1 (from 3.06 to 1.86 s), T2 (from 0.137 to 0.033 s) and proton density values of labeled scaffolds were also detected with increased molar ratios of Gd-DTPA in BPLPMGd scaffolds (FIGS. 4(b), 4(c), and 4(d)).

In Vitro Cell Culture Studies

Figure 5A:
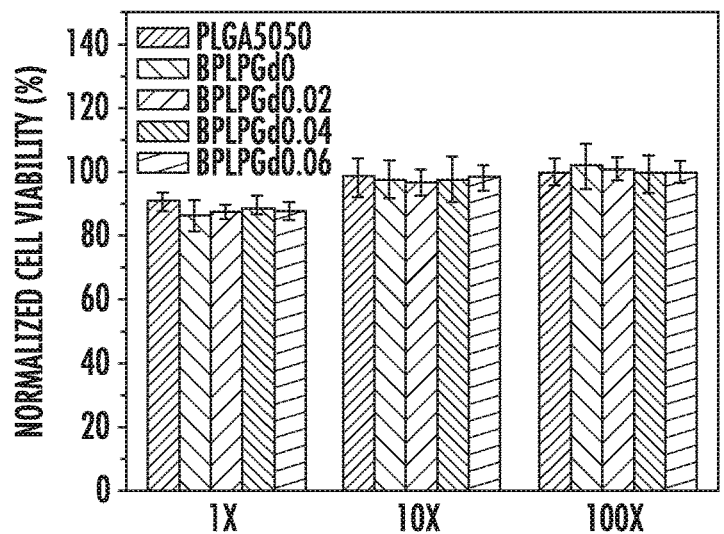
FIG. 5(a) is a graph of in vitro cell (3T3 fibroblast) culture studies of cytotoxicity of material degradation products.
Figure 5B:
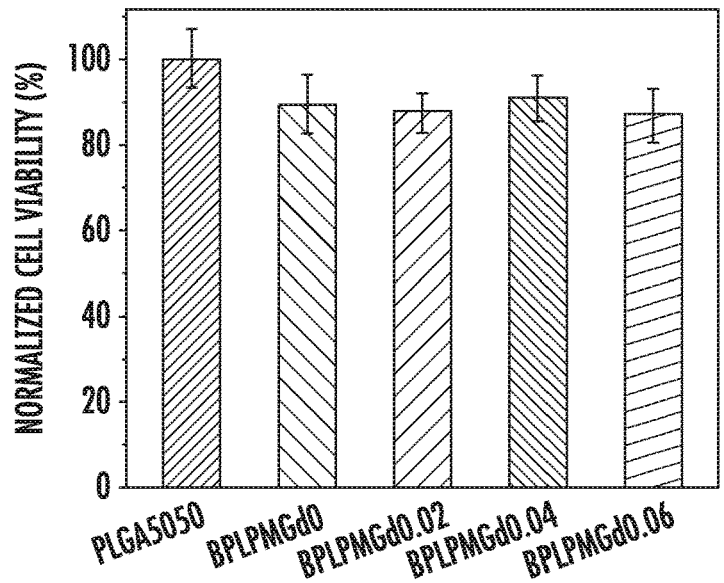
FIG. 5(b) is a graph of in vitro cell (3T3 fibroblast) culture studies of cytotoxicity of polymer films.
Figure 5C:
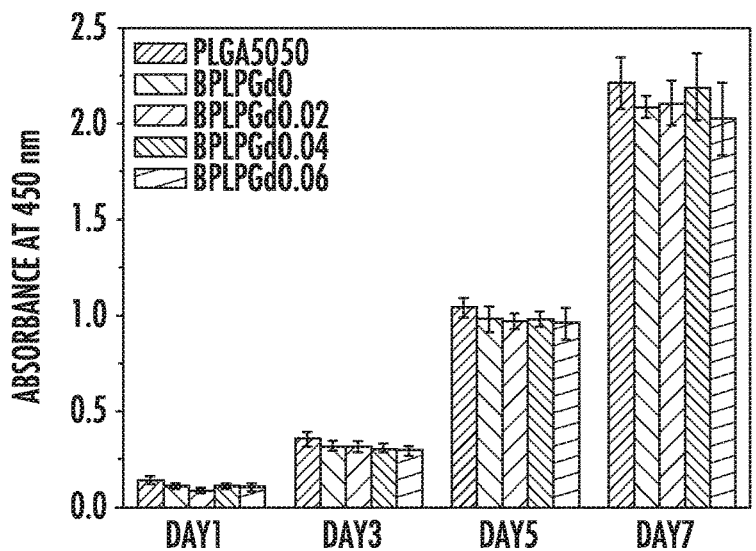
FIG. 5(c) is a graph of in vitro cell (3T3 fibroblast) culture studies of cell proliferation on polymer films.
Figure 5D:
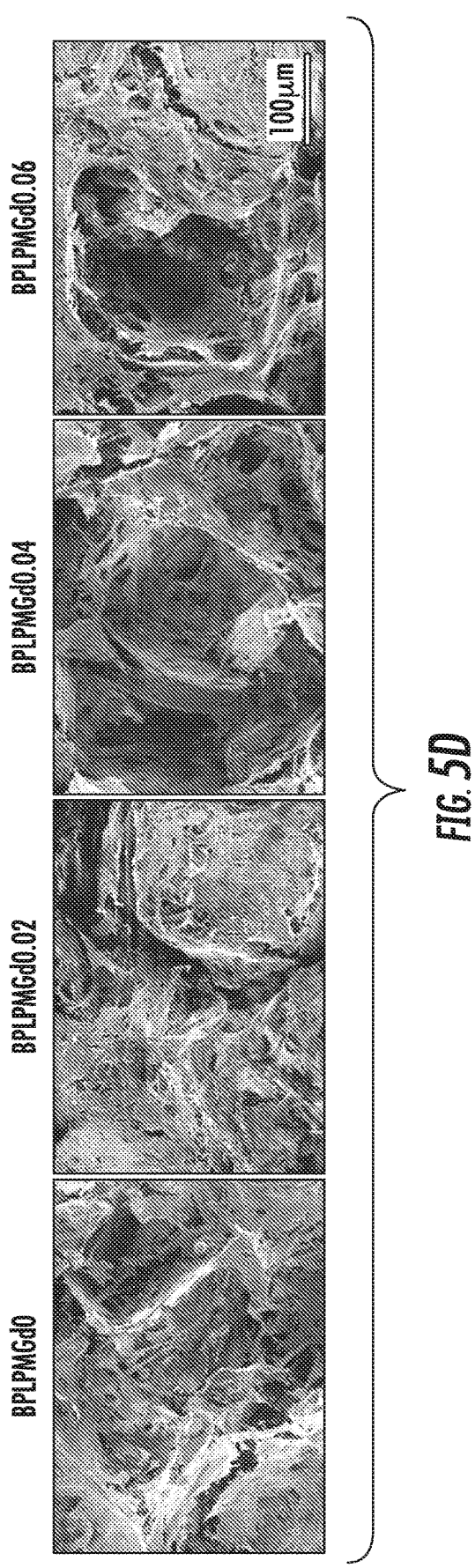
FIG. 5(d) is SEM images of BPLPMGd scaffolds with 3T3 fibroblast cells cultured for 7 days.

In cytotoxicity study of degradation products, the results indicate that after 10 times dilution of the original concentration (0.1 g/ml in 1M NaOH), all degradation products are nontoxic (FIG. 5(a)). BPLPMGd films present comparable cytocompatibility as PLGA5050 in the cytotoxicity study of polymer films (FIG. 5(b)). In cell proliferation study, 3T3 fibroblasts were cultured on BPLPMGd films (BPLPMGd0, BPLPMGd0.02, BPLPMGd0.04, and BPLPMGd0.06) for 7 days. The results in FIG. 5(c) suggest that BPLPMGd films are able to successfully promote the proliferation of 3T3 cells. In Figure and 5(d), SEM images present that 3T3 cells are able to cover the surface very well and penetrate deep into the porous scaffold after being cultured for 7 days. In vitro cell culture studies confirmed the cytocompatibility of BPLPMGd degradation products and BPLPMGd films, as well as the capacity of promoting the proliferation of 3T3 fibroblasts of BPLPMGd films and scaffolds.

In Vivo Fluorescence Imaging

Figure 6:
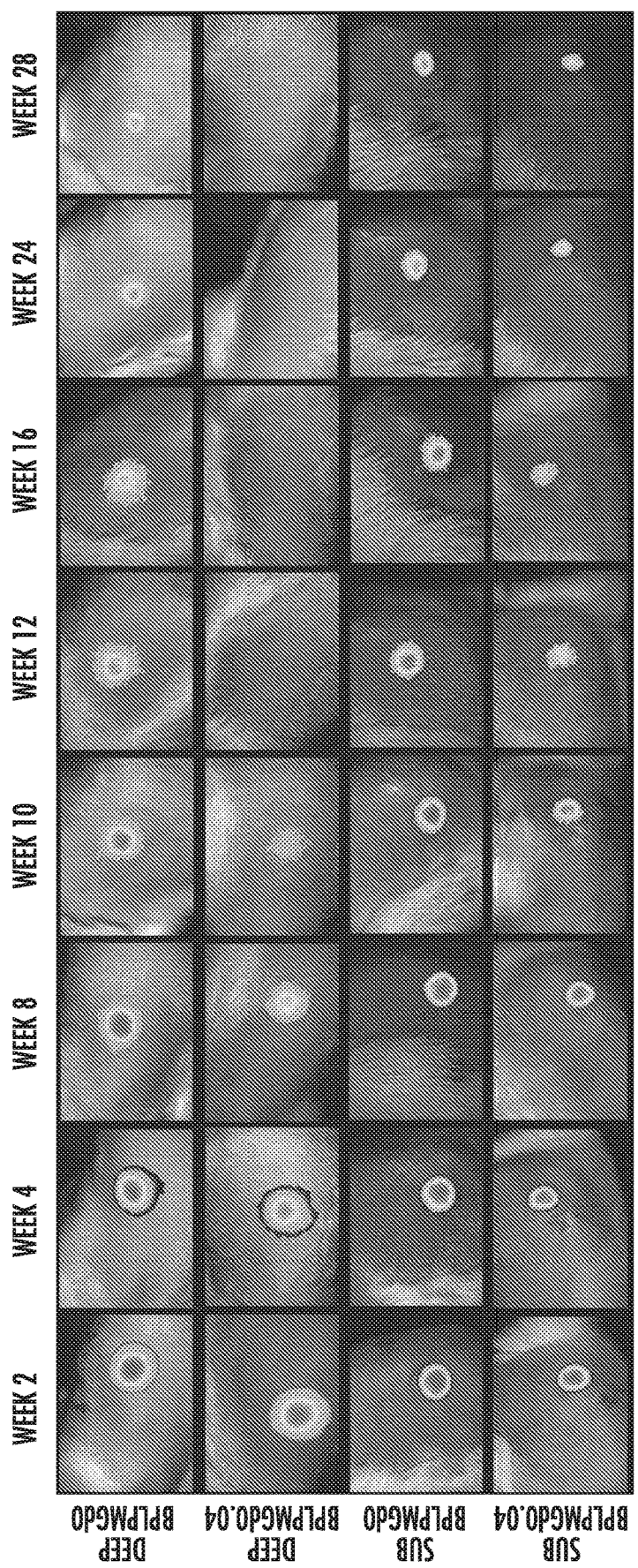
FIG. 6 includes fluorescent intensity maps (excitation wavelength of 704 nm) of deep tissue and subcutaneously implanted BPLPMGd scaffolds at different implantation time points.
Figure 7:
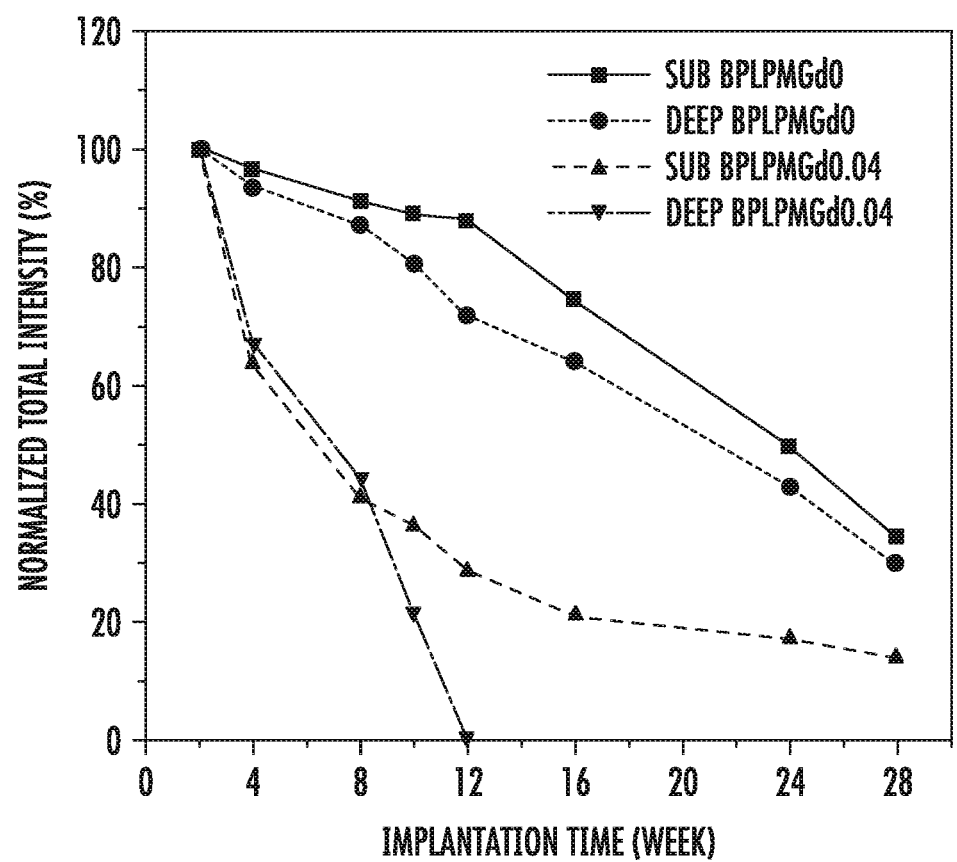
FIG. 7 is a graph of normalized total fluorescent intensity changes of implanted BPLPMGd scaffolds.

In animal studies, BPLPMGd0 and BPLPMGd0.04 porous scaffolds were chosen for subcutaneous and deep tissue implantations for 28 weeks. For subcutaneously implanted BPLPMGd0 and BPLPMGd0.04 scaffolds, both visible (595 nm) and NIR (704 and 735 nm) lights could be applied as excitation lights to generate fluorescent images to detect the localization and degradation of scaffolds. However, only NIR lights (704 and 735 nm) were able to penetrate deep enough to monitor scaffolds that implanted under deep muscle tissues. At the excitation wavelength of 704 nm, by systematically comparing the fluorescence intensity maps and quantitatively calculating the total fluorescence intensity changes of applied scaffolds, it is possible to estimate degradation profiles and rates of the scaffolds (FIG. 6 and FIG. 7). The results indicated that BPLPMGd0.04 scaffolds implanted under deep tissues degrade the fastest, then followed by BPLPMGd0.04 scaffolds implanted subcutaneously, BPLPMGd0 scaffolds implanted under deep tissues, and BPLPMGd0 scaffolds implanted subcutaneously.

In Vivo MR Imaging

Figure 8:
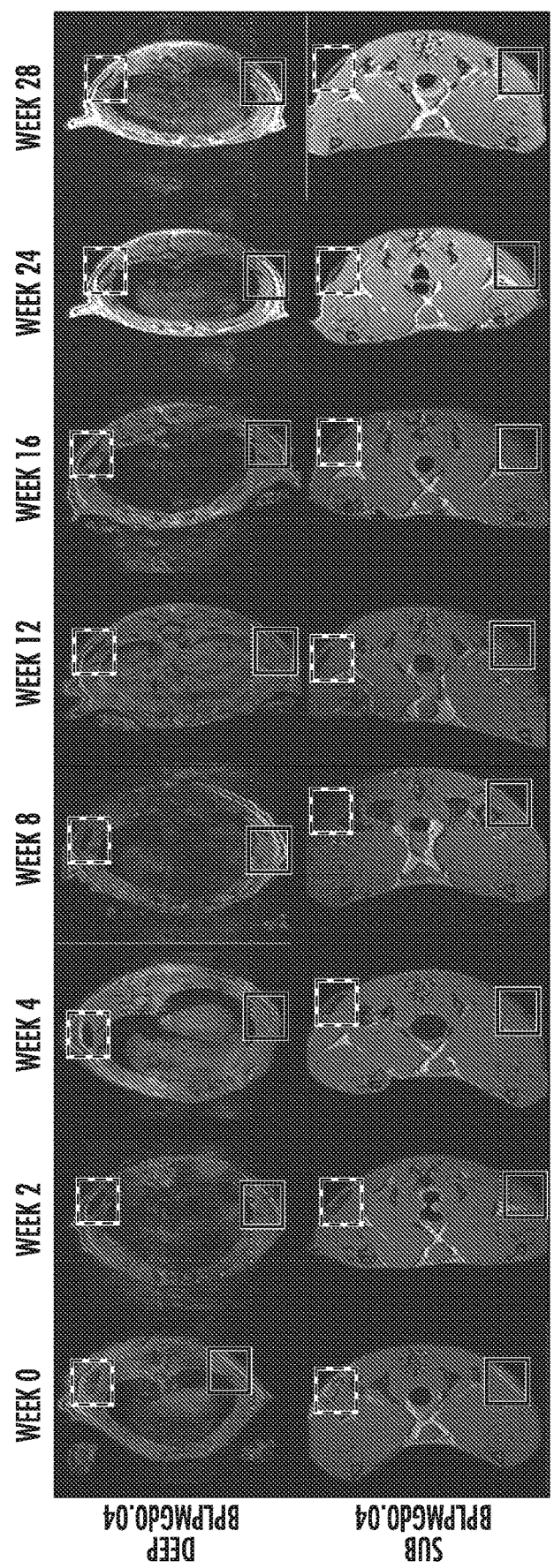
FIG. 8 includes in vivo MRI images of deep tissue and subcutaneously implanted BPLPMGd scaffolds (only BPLPMGd 0.04 groups are visible).
Figure 9A:
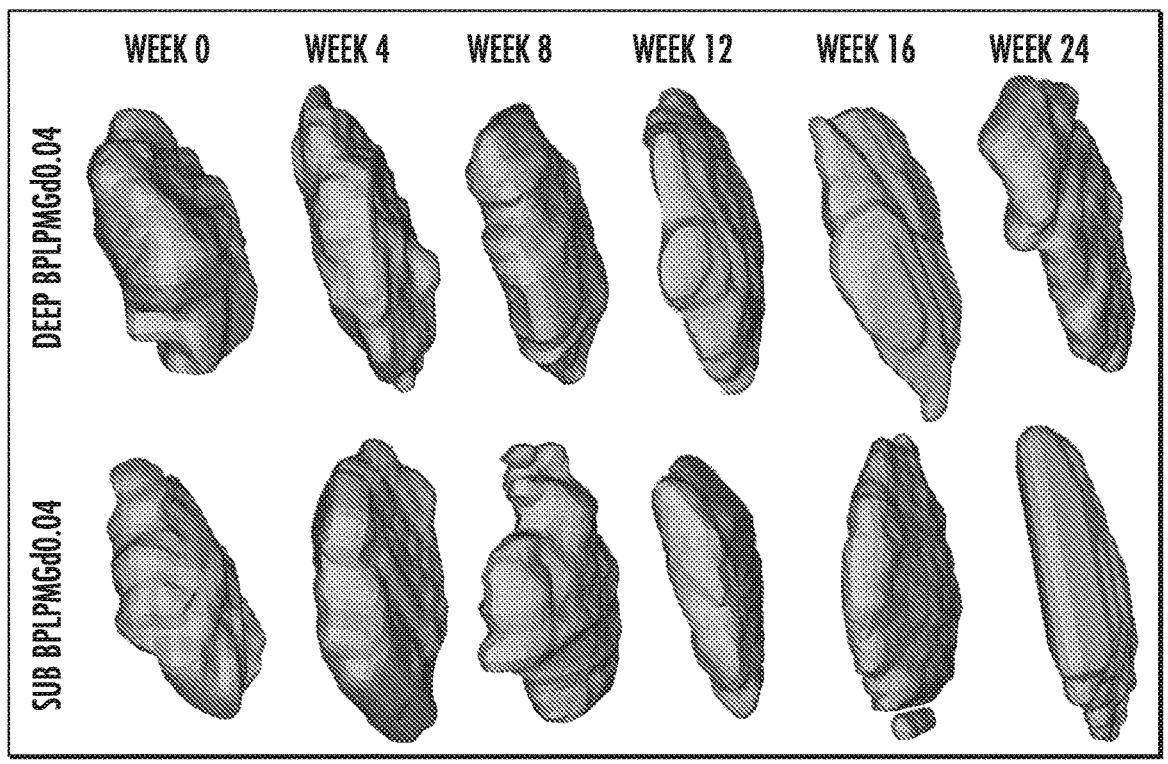
FIG. 9(a) is 3D images of deep tissue and subcutaneously implanted BPLPMGd0.04 scaffolds over time.
Figure 9B:
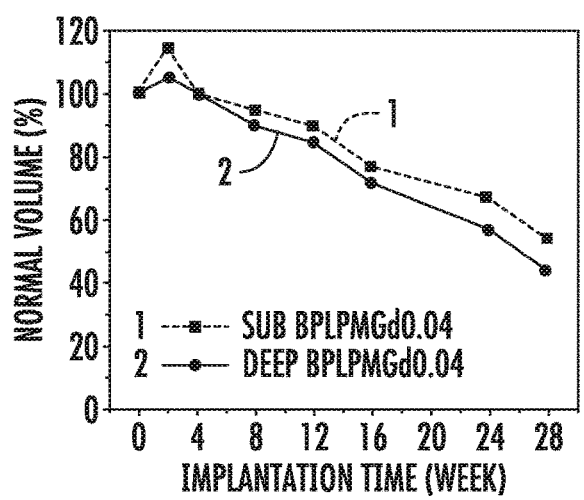
FIG. 9(b) is a graph of normalized volume changes of deep tissue and subcutaneously implanted BPLPMGd0.04 scaffolds over time.
Figure 9C:
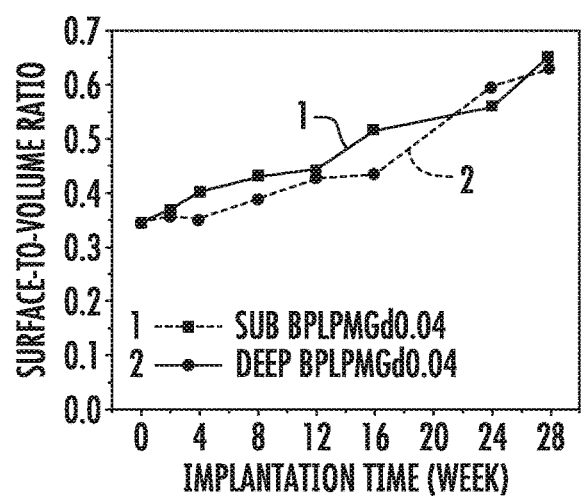
FIG. 9(c) is a graph of surface-to-volume ratio changes of deep tissue and subcutaneously implanted BPLPMGd0.04 scaffolds over time.
Figure 10A:
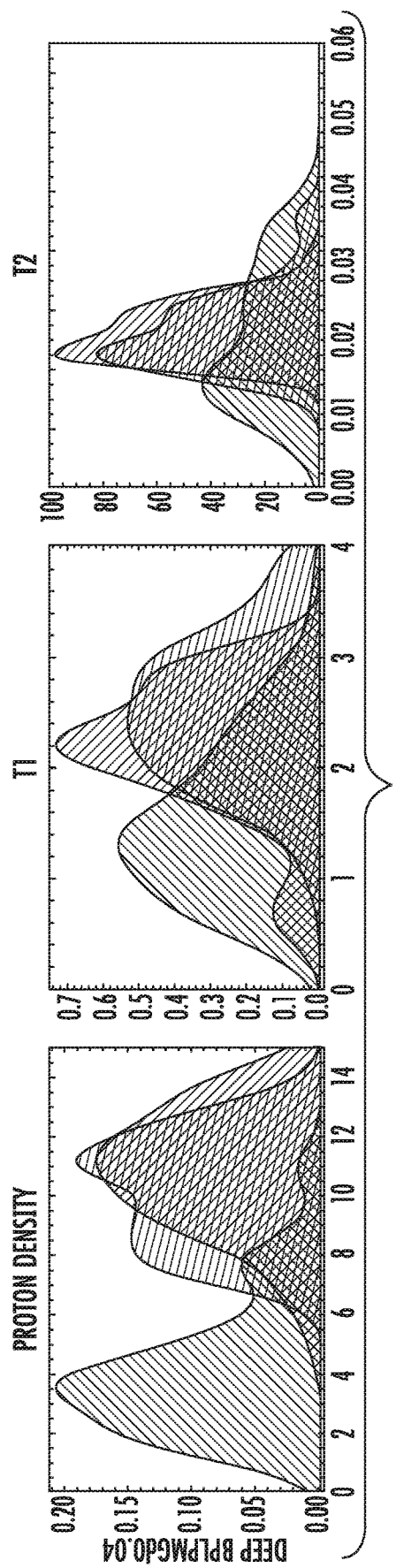
FIG. 10(a) is graphs of proton density, T1 value distributions, and T2 value distributions of deep tissue implanted BPLPMGd0.04 scaffolds vs. tissues near and far away from them.
Figure 10B:
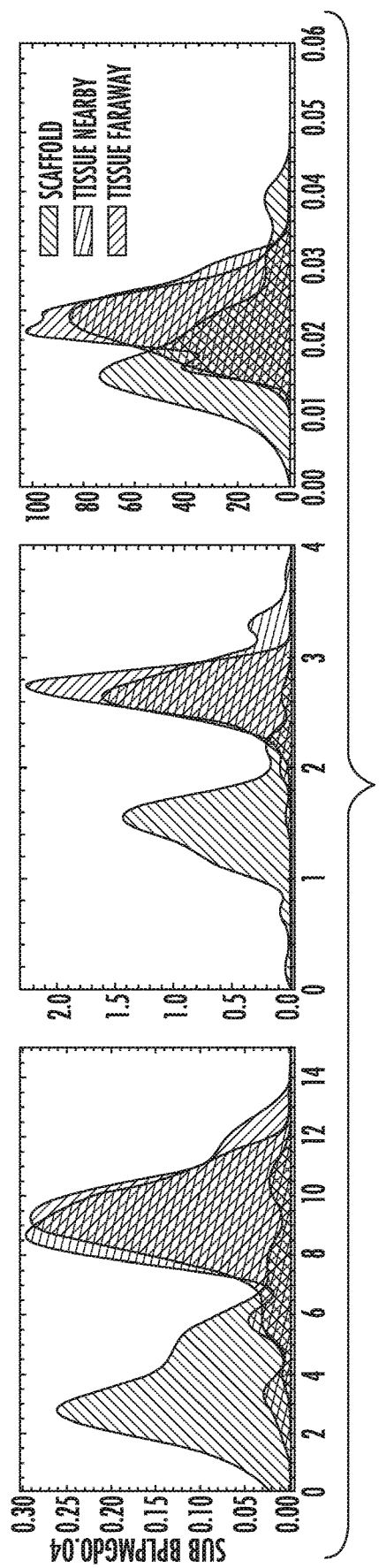
FIG. 10(b) is graphs of Proton density, T1 value and T2 value distributions of subcutaneously implanted BPLPMGd0.04 scaffolds vs. tissues nearby and far away from them.

FIG. 8 presents in vivo MRI images of deep tissue and subcutaneously implanted BPLPMGd scaffolds. The results exhibit that only BPLPMGd0.04 groups are visible, while BPLPMGd0.04 scaffolds that have no contrast agents are not able to be detected through MRI. Combining softwares of MATLAB, Mathematica, ITK-SNAP and STL Viewer, 3D structures of BPLPMGd0.04 scaffolds were acquired, from which the decreased sizes and various shapes of scaffolds were presented (FIG. 9(a)). In addition, accurate volume and surface-to-volume ratio changes of BPLPMGd0.04 scaffolds overtime were also obtained (FIGS. 9(b), 9(c), and 9(d)). Furthermore, the proton density, T1 and T2 value distributions of implanted BPLPMGd0.04 scaffolds as well as tissues nearby and far away from them were quantitatively studied. As presented in FIGS. 10(a) and 10(b), proton density, T1 and T2 value distributions of implanted BPLPMGd0.04 scaffolds are able to be easily distinguished from tissues nearby and far away from them, which indicate significantly contrast effects of the scaffolds.

In Vivo Foreign Body Reaction Study

Figure 11:
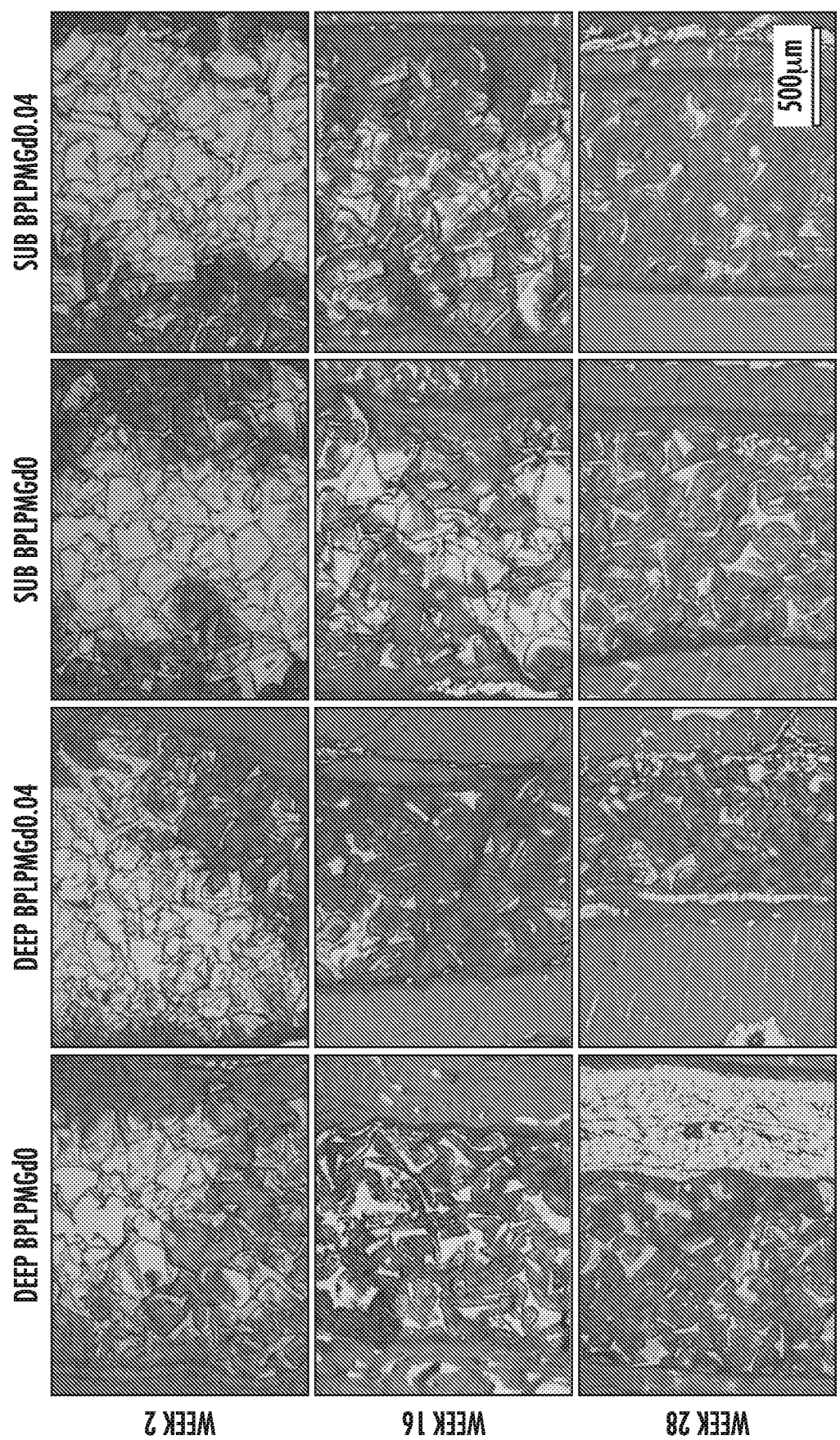
FIG. 11 includes Hematoxylin and eosin (H&E) staining images of sections of deep tissue and subcutaneously implanted BPLPMGd scaffolds.
Figure 12:
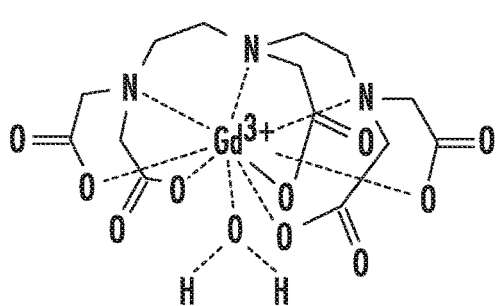
FIG. 12 shows structures of some MRI contrast agents described herein.
Figure 12:
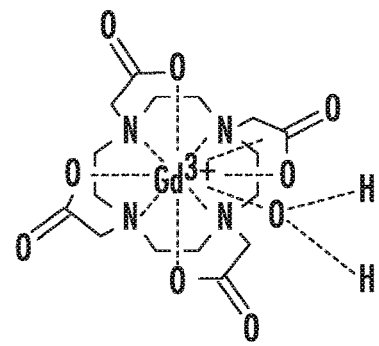
Figure 12:
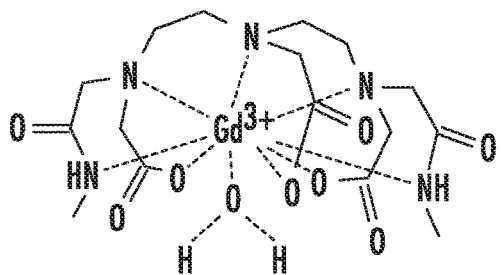
Figure 12:
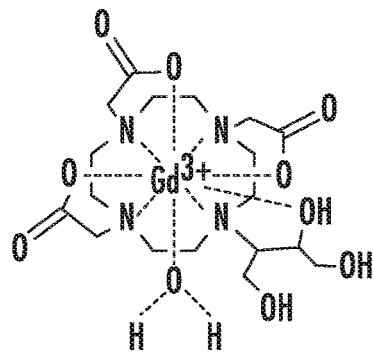
Figure 12:
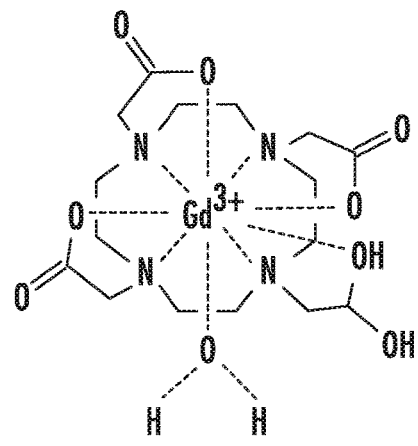
Figure 13:
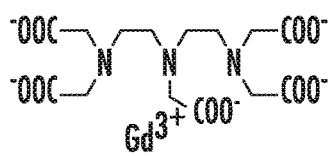
FIG. 13 shows structures of some Gd complexes used as MRI contrast agents described herein.
Figure 13:
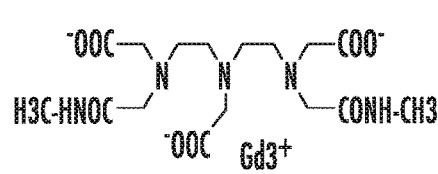
Figure 13:
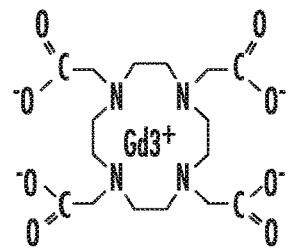
Figure 13:
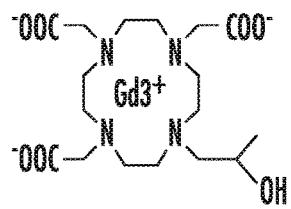
Figure 13:
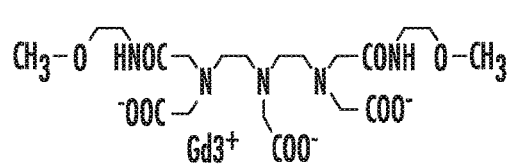
Figure 13:
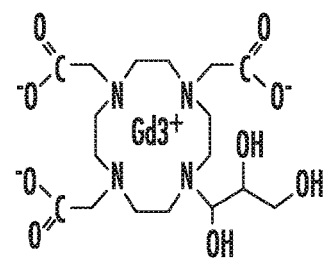
Figure 13:
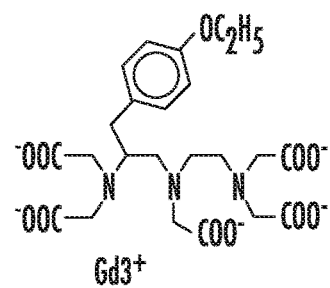
Figure 13:
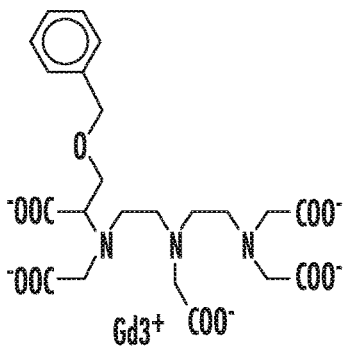
Figure 13:
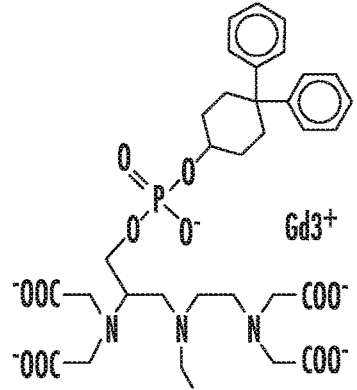
Figure 14:
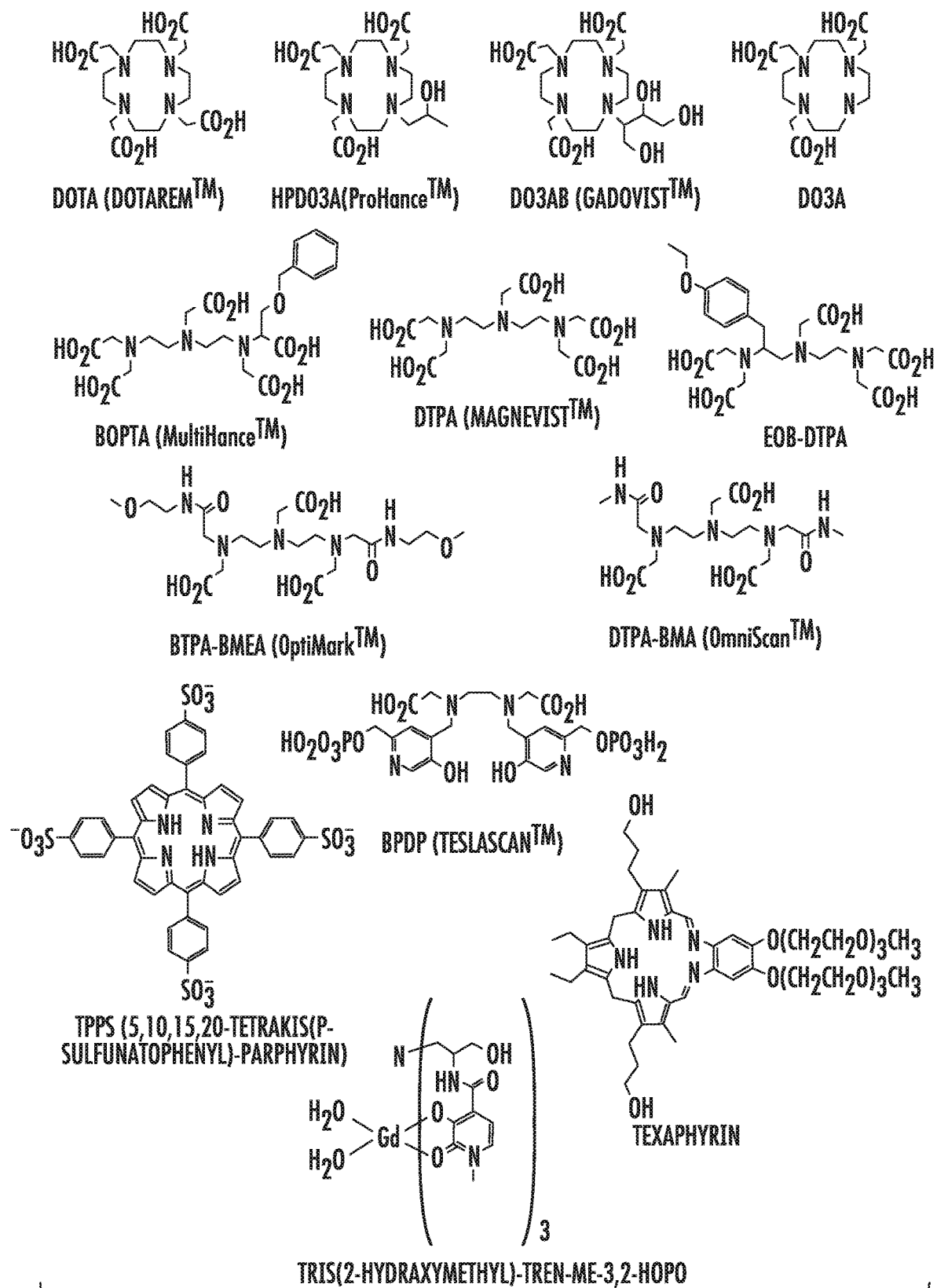
FIG. 14 shows structures of some lanthanide ligands and Gd complexes according to some embodiments described herein.
Figure 15:
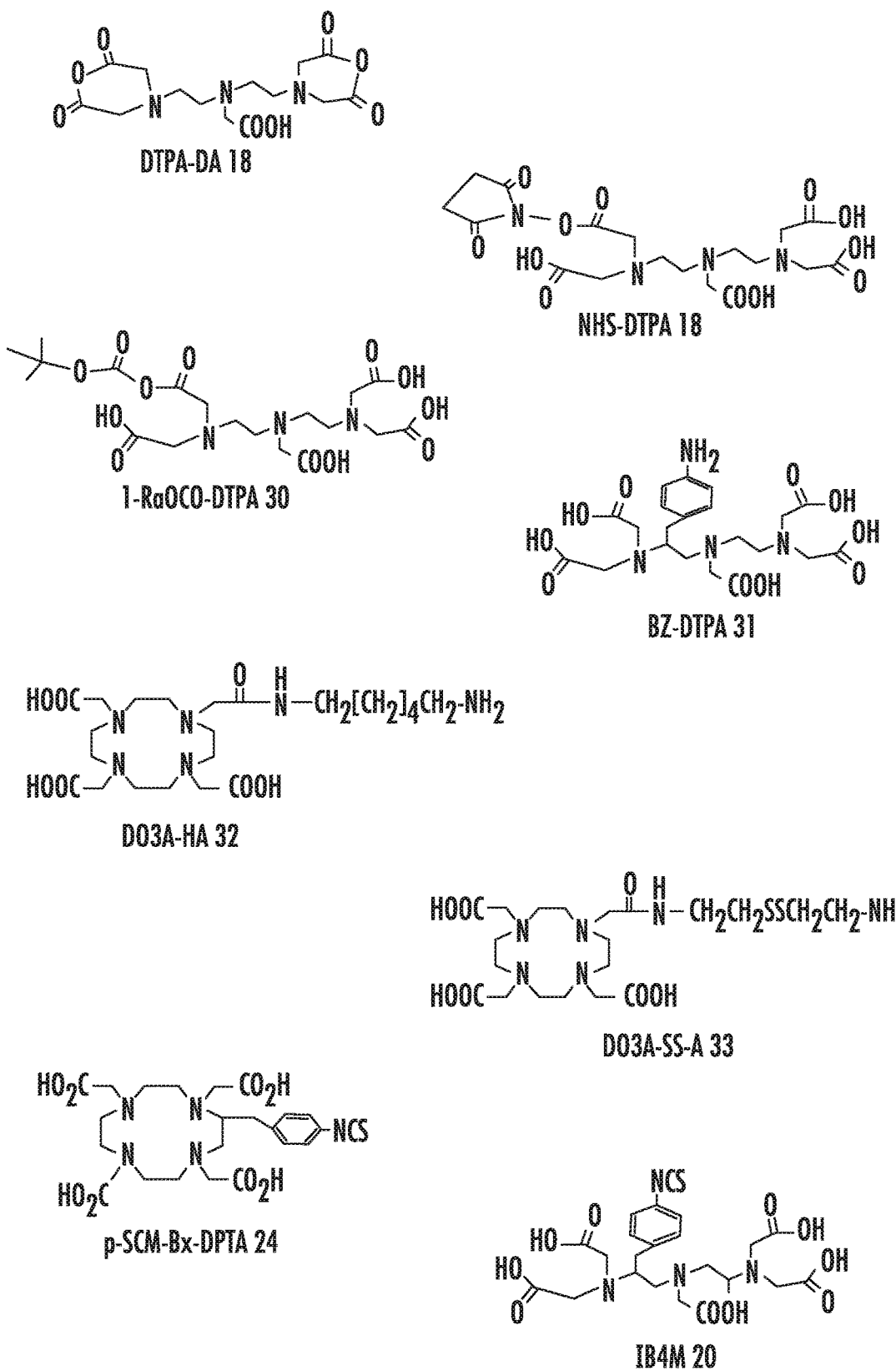
FIG. 15 shows the structures of bifunctional MRI contrast agents and/or ligands according to some embodiments described herein.
Figure 16:
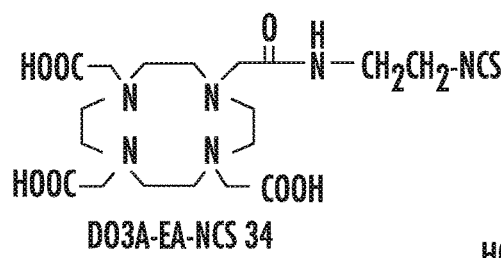
FIG. 16 shows the structures of bifunctional MRI contrast agents and/or ligands according to some embodiments described herein.
Figure 16:
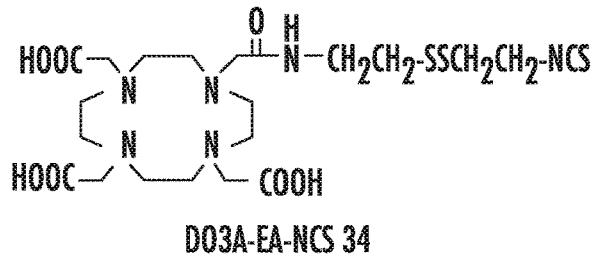
Figure 16:
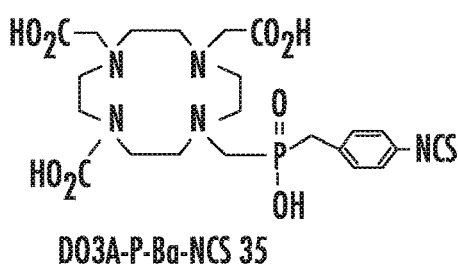
Figure 16:
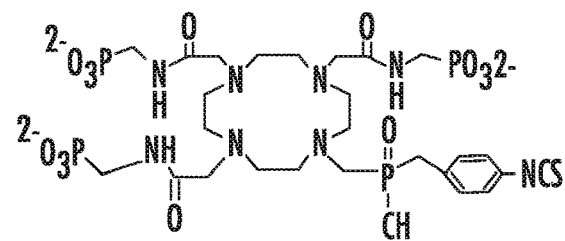
Figure 16:
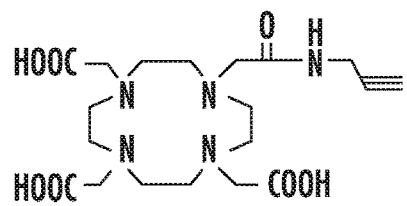
Figure 16:
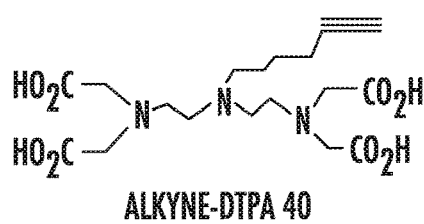
Figure 16:
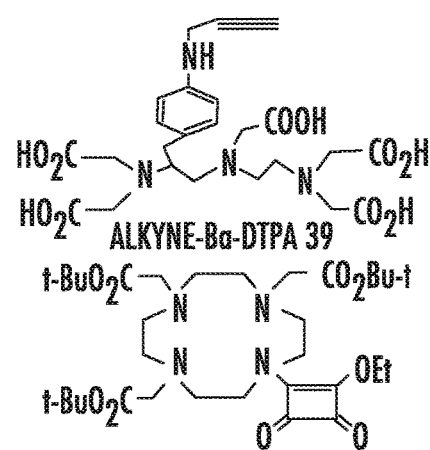

The in vivo foreign body response of BPLPMGd scaffolds was studied by hematoxylin and eosin (H&E) staining of sections of deep tissue and subcutaneously implanted BPLPMGd0 and BPLPMGd0.04 scaffolds. As shown in FIG. 11, as the surrounding cells gradually penetrate into the scaffolds, the implanted BPLPMGd scaffolds degrade correspondingly. Moreover, the in vivo degradation properties of scaffolds are demonstrated by the H&E staining that BPLPMGd0.04 scaffolds implanted under deep tissue degrade the fastest, and BPLPMGd0 scaffolds implanted subcutaneously degrade the slowest.

5. Conclusion

The newly designed fluorescence and MR dual imaging biodegradable materials (BPLPMGds) enabled unprecedented deep tissue 3D imaging, as well as in-situ quantitative studies of locations, shapes, volumes, and degradation properties of implanted scaffolds. The significant data supports the feasibility of synthesis and utility of the dual-imaging enabled platform biodegradable polymers, BPLPMGds. The fluorescence/MR dual imaging capabilities of BPLPMGd polymers will help better understand the materials design and secure unprecedented in-situ real-time materials/cell/tissue interactions and substantially expand the capabilities and applications of the polymers in regenerative medicine and cancer diagnosis and treatment. BPLPMGd polymers are new and unique and may open new avenues in new material design and applications to greatly facilitate the marriage of modern biomedical imaging technologies with medical implant technologies for regenerative engineering.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention

The invention claimed is:

1. A composition comprising:
a polymer or oligomer formed from first reacting:
a) one or more monomers of Formula (A1) and optionally one or more monomers of Formula (A2);
b) one or more monomers of Formula (B1) or (B2);
c) one or more monomers of Formula (F);
d) one or more monomers comprising an MRI contrast agent of Formula (J1), (J2), (J3), (J4), (J5), or (J6), and optionally one or more other reactants or monomers;
such that the polymer or oligomer has the one or more monomers comprising an MRI contrast agent as a part of a backbone of the polymer or oligomer,
wherein the one or more monomers comprising an MRI contrast agent participate in a condensation polymerization reaction to form the polymer or oligomer;
wherein the formed polymer or oligomer is then cross-linked to form a polymer network,

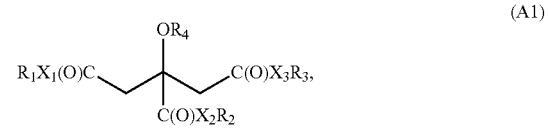

(A1)

-continued

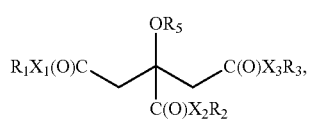 (A2)

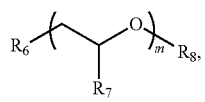 (B1)

 (B2)

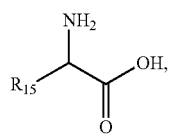 (F)

HO-[M]-OH (J1),

HOOC-[M]-COOH (J2),

H₂N-[M]-NH₂ (J3),

HO-[M]-COOH (J4),

HO-[M]-NH₂ (J5),

HOOC-[M]-NH₂ (J6), wherein $X_1$, $X_2$, and $X_3$ are each independently O or NH;
$R_1$, $R_2$, and $R_3$ are each independently H, a C1 to C22 alkyl or alkenyl group, or $M^+$;
R4 is H, a C1 to C22 alkyl or alkenyl group, or $M^+$;
$R_5$ is $C(O)R_{23}$;
$M^+$ is a monovalent metal cation;
$R_6$ is H, $NH_2$, OH, $OCH_3$, $OCH_2CH_3$, $CH_3$, or $CH_2CH_3$;
$R_7$ is H or a C1 to C23 alkyl or alkenyl group;
$R_8$ is H, a C3 to C22 alkyl or alkenyl group, $CH_2CH_2OH$, or $CH_2CH_2NH_2$;
$R_{15}$ is an amino acid side chain;
$R_{23}$ is a C14 to C22 alkyl or alkenyl group;
[M] is a metal-containing portion of the MRI contrast agent;
wherein n is integer ranging from 2 to 20 and
m is integer ranging from 1 to 20.

2. The composition of claim 1, wherein the polymer or oligomer is formed by reacting:
   a) the one or more monomers of Formula (A1) and optionally the one or more monomers of Formula (A2);
   b) the one or more monomers of Formula (B1) or (B2);
   c) the one or more monomers of Formula (F);
   d) the one or more monomers comprising the MRI contrast agent of Formula (J1), (J2), (J3), (J4), (J5), or (J6);
   and
   e) one or more monomers of Formula (K):

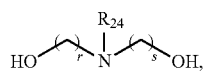 (K)

wherein $R_{24}$ is H or a C1 to C20 alkyl or alkenyl group; and r and s are each independently an integer between 0 and 20.

3. The composition of claim 1, wherein the polymer or oligomer is formed by reacting:
   a) the one or more monomers of Formula (A1) and optionally the one or more monomers of Formula (A2);
   b) the one or more monomers of Formula (B1) or (B2);
   c) the one or more monomers of Formula (F);
   d) the one or more monomers comprising the MRI contrast agent of Formula (J1), (J2), (J3), (J4), (J5), or (J6); and
   e) one or more monomers of Formula (C), Formula (D1), Formula (D2), Formula (D3), Formula (D4), Formula (E1), Formula (E2), Formula (G), Formula (H1), Formula (H2), Formula (H3), Formula (I1), Formula (I2), Formula (I3), Formula (I4), Formula (I5), and/or Formula (I6):

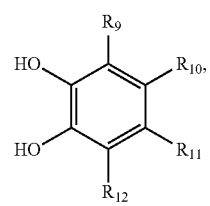 (C)

 (D1)

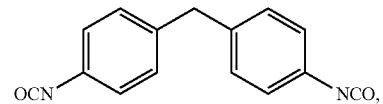 (D2)

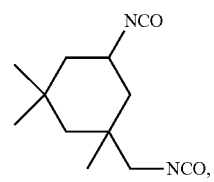 (D3)

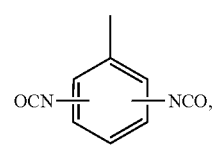 (D4)

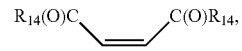 (E1)

 (E2)

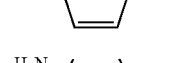 (G)

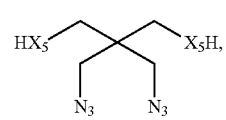 (H1)

-continued

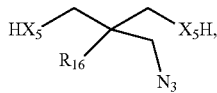
(H2)

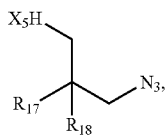
(H3)

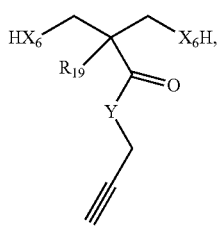
(I1)

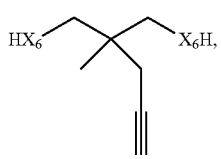
(I2)

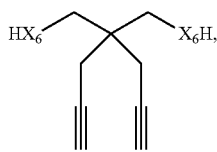
(I3)

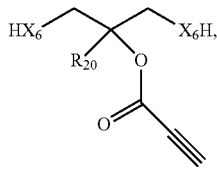
(I4)

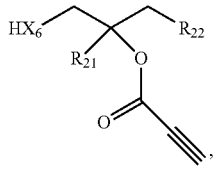
(I5)

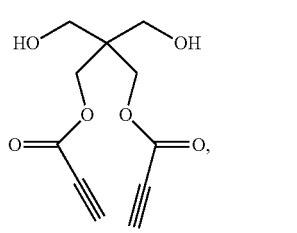
(I6)

wherein $R_9$, $R_{10}$, $R_{11}$, and $R_{12}$ are each independently H, OH, $CH_2(CH_2)_xNH_2$, $CH_2(CHR_{13})NH_2$, $CH_2(CH_2)_xOH$, $CH_2(CHR_{13})OH$, or $CH_2(CH_2)_xCOOH$;
$R_{13}$ is COOH or $(CH_2)_yCOOH$;
x is an integer ranging from 0 to 10;
y is an integer ranging from 1 to 10;
p is an integer ranging from 1 to 10;
$R_{14}$ is OH, $OCH_3$, $OCH_2CH_3$, or Cl;
$R_{15}$ is an amino acid side chain;
q is an integer ranging from 1 to 20;

$X_5$ is O or NH;
$R_{16}$ is $CH_3$ or $CH_2CH_3$,
$R_{17}$ and $R_{18}$ are each independently $CH_2N_3$, $CH_3$, or $CH_2CH_3$,
$X_6$ and Y are each independently O or NH;
$R_{19}$ and $R_{20}$ are each independently $CH_3$ or $CH_2CH_3$,
$R_{21}$ is $O(CO)C\equiv CH$, $CH_3$, or $CH_2CH_3$; and
$R_{22}$ is $CH_3$, OH or $NH_2$.

4. The composition of claim 3, wherein the polymer or oligomer is formed from one or more monomers comprising one or more alkyne moieties or one or more azide moieties.

5. The composition of claim 4, wherein the polymer or oligomer is formed from one or more monomers comprising one or more azide moieties, and the one or more monomers comprising one or more azide moieties comprises a monomer of Formula (H1), (H2), or (H3).

6. The composition of claim 4, wherein the polymer or oligomer is formed from one or more monomers comprising one or more alkyne moieties, and the one or more monomers comprising one or more alkyne moieties comprises a monomer of Formula (I1), (I2), (I3), (I4), (I5), or (I6).

7. The composition of claim 4, wherein the one or more monomers comprising one or more alkyne moieties or one or more azide moieties comprises a peptide, polypeptide, nucleic acid, or polysaccharide.

8. The composition of claim 1, wherein the polymer or oligomer is luminescent and MRI-sensitive.

9. The composition of claim 8, wherein the polymer or oligomer is luminescent in the near-infrared region.

10. The composition of claim 1, wherein the polymer or oligomer is biodegradable.

11. A method of imaging a biological environment comprising:
disposing the composition of claim 1 in the biological environment.

12. The method of claim 11 further comprising:
exposing the biological environment to electromagnetic radiation having a wavelength corresponding to an excitation wavelength of a luminescent moiety of the polymer or oligomer of the composition; and
detecting light emitted by the luminescent moiety.

13. The method of claim 11, further comprising:
exposing the biological environment to radio-frequency electromagnetic radiation while the biological environment is disposed in a magnetic field, thereby exciting hydrogen atoms of the biological environment; and
detecting relaxation of the excited hydrogen atoms.

14. A scaffold comprising the composition of claim 1.

15. A graft comprising the composition of claim 1.

16. A film comprising the composition of claim 1.

17. The composition of claim 1, wherein the one or more monomers comprising the MRI contrast agent are bonded to the backbone of the polymer or oligomer through OH and/or COOH moieties.

18. The composition of claim 1, wherein the one or more monomers comprising the MRI contrast agent are a part of a backbone of the polymer or oligomer as a result of a polycondensation reaction between a), b), c), and d).

19. The composition of claim 1, wherein the polymer or oligomer comprises at least about 5 wt % of MRI contrast agent moiety based on the total number of moles of the comonomers of the polymer or oligomer.

20. The composition of claim 1, wherein the metal-containing portion of the MRI contrast agent comprises a lanthanide-ion containing portion.

21. The composition of claim 20, wherein the lanthanide-ion containing portion comprises a lanthanide metal ion of Gd, Nd, Sm, Eu, Tb, Dy, Ho, or Er.

22. The composition of claim 20, wherein the lanthanide-ion containing portion comprises $Gd^{3+}$.

* * * * *